(12) United States Patent
McClain et al.

(10) Patent No.: US 11,039,943 B2
(45) Date of Patent: Jun. 22, 2021

(54) BIOABSORBABLE BIOMEDICAL IMPLANTS

(71) Applicant: Micell Technologies, Inc., Durham, NC (US)

(72) Inventors: James B. McClain, Raleigh, NC (US); Charles Douglas Taylor, Franklinton, NC (US)

(73) Assignee: Micell Technologies, Inc., Durham, NC (US)

( * ) Notice: Subject to any disclaimer, the term of this patent is extended or adjusted under 35 U.S.C. 154(b) by 0 days.

(21) Appl. No.: 14/207,336

(22) Filed: Mar. 12, 2014

(65) Prior Publication Data

US 2014/0277401 A1    Sep. 18, 2014

Related U.S. Application Data

(60) Provisional application No. 61/777,230, filed on Mar. 12, 2013.

(51) Int. Cl.
| | | |
|---|---|---|
| *A61F 2/86* | (2013.01) | |
| *A61L 31/10* | (2006.01) | |
| *A61L 31/16* | (2006.01) | |
| *A61L 31/06* | (2006.01) | |
| *A61L 31/14* | (2006.01) | |

(52) U.S. Cl.
CPC ............. *A61F 2/86* (2013.01); *A61L 31/06* (2013.01); *A61L 31/10* (2013.01); *A61L 31/16* (2013.01); *A61F 2210/0004* (2013.01); *A61F 2250/0035* (2013.01); *A61F 2250/0067* (2013.01); *A61L 31/148* (2013.01); *A61L 2300/416* (2013.01)

(58) Field of Classification Search
CPC ........ A61F 2/06; A61F 2/07; A61F 2240/001; A61F 2250/001; A61F 2/86; A61F 2210/0004; A61F 2250/0067; A61F 2/90; A61F 2/9522; A61F 2250/003; A61F 2250/0068; A61F 2/89; A61F 2210/0076; A61F 2/82; A61F 2/915; A61F 2002/30062; A61F 2002/30677; A61F 2310/0097; A61L 31/16; A61L 2300/216; A61L 2300/416; A61L 2300/606; A61L 2300/608; A61L 2300/63; A61L 2420/02; A61L 2420/06; A61L 2420/08; A61L 31/10; A61L 31/148; A61L 2300/42; A61L 2300/602
See application file for complete search history.

(56) References Cited

U.S. PATENT DOCUMENTS

| | | |
|---|---|---|
| 3,087,860 A | 4/1963 | Endicott |
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |

(Continued)

FOREIGN PATENT DOCUMENTS

| | | |
|---|---|---|
| CA | 2237466 A1 | 11/1998 |
| CA | 2589761 | 12/2004 |

(Continued)

OTHER PUBLICATIONS

Abreu Filho et al., "Influence of metal alloy and the profile of coronary stents in patients with multivessel coronary disease," CLINICS 66(6):985-989 (2011).

(Continued)

*Primary Examiner* — Seema Mathew
(74) *Attorney, Agent, or Firm* — Lerner, David, Littenberg, Krumholz & Mentlik, LLP

(57) ABSTRACT

A bioabsorbable biomedical implant is disclosed. The implant includes a tubular scaffold comprising a plurality of interconnected polymer struts. The interconnected polymer struts defines a plurality of deformable cells. The polymer struts have an average thickness of no more than 120 μm. Methods for making the bioabsorbable biomedical implant, including the methods for making the polymer materials for the tubular scaffold, are also disclosed.

8 Claims, No Drawings

(56) References Cited

U.S. PATENT DOCUMENTS

| | | | |
|---|---|---|---|
| 5,324,049 | A | 6/1994 | Mistrater et al. |
| 5,340,614 | A | 8/1994 | Perman et al. |
| 5,350,361 | A | 9/1994 | Tsukashima et al. |
| 5,350,627 | A | 9/1994 | Nemphos et al. |
| 5,342,621 | A | 10/1994 | Eury |
| 5,356,433 | A | 10/1994 | Rowland et al. |
| 5,360,403 | A | 11/1994 | Mische |
| 5,362,718 | A | 11/1994 | Skotnicki et al. |
| 5,366,504 | A | 11/1994 | Andersen et al. |
| 5,368,045 | A | 11/1994 | Clement et al. |
| 5,372,676 | A | 12/1994 | Lowe |
| 5,385,776 | A | 1/1995 | Maxfield et al. |
| 5,387,313 | A | 2/1995 | Thoms |
| 5,403,347 | A | 4/1995 | Roby et al. |
| 5,470,603 | A | 11/1995 | Staniforth et al. |
| 5,494,620 | A | 2/1996 | Liu et al. |
| 5,500,180 | A | 3/1996 | Anderson et al. |
| 5,545,208 | A | 8/1996 | Wolff et al. |
| 5,556,383 | A | 9/1996 | Wang et al. |
| 5,562,922 | A | 10/1996 | Lambert |
| 5,569,463 | A | 10/1996 | Helmus et al. |
| 5,570,537 | A | 11/1996 | Black et al. |
| 5,578,709 | A | 11/1996 | Woiszwillo |
| 5,599,576 | A | 2/1997 | Opolski |
| 5,605,696 | A | 2/1997 | Eury et al. |
| 5,607,442 | A | 3/1997 | Fischell et al. |
| 5,609,629 | A | 3/1997 | Fearnot et al. |
| 5,626,611 | A | 5/1997 | Liu et al. |
| 5,626,862 | A | 5/1997 | Brem et al. |
| 5,632,772 | A | 5/1997 | Alcime et al. |
| 5,669,932 | A | 9/1997 | Fischell et al. |
| 5,674,192 | A | 10/1997 | Sahatjian et al. |
| 5,674,242 | A | 10/1997 | Phan et al. |
| 5,674,286 | A | 10/1997 | D'Alessio et al. |
| 5,725,570 | A | 3/1998 | Heath |
| 5,733,303 | A | 3/1998 | Israel et al. |
| 5,766,158 | A | 6/1998 | Opolski |
| 5,800,511 | A | 9/1998 | Mayer |
| 5,807,404 | A | 9/1998 | Richter |
| 5,811,032 | A | 9/1998 | Kawai et al. |
| 5,824,049 | A | 10/1998 | Ragheb et al. |
| 5,837,313 | A | 11/1998 | Ding et al. |
| 5,843,120 | A | 12/1998 | Israel et al. |
| 5,871,436 | A | 2/1999 | Eury |
| 5,873,904 | A | 2/1999 | Ragheb et al. |
| 5,876,426 | A | 3/1999 | Kume et al. |
| 5,876,452 | A * | 3/1999 | Athanasiou ............... A61F 2/28 424/424 |
| 5,913,895 | A | 6/1999 | Burpee et al. |
| 5,924,631 | A | 7/1999 | Rodrigues et al. |
| 5,948,020 | A | 9/1999 | Yoon et al. |
| 5,957,975 | A | 9/1999 | Lafont et al. |
| 5,981,568 | A | 11/1999 | Kunz et al. |
| 5,981,719 | A | 11/1999 | Woiszwillo et al. |
| 6,013,855 | A | 1/2000 | McPherson et al. |
| 6,036,978 | A | 3/2000 | Gombotz et al. |
| 6,039,721 | A | 3/2000 | Johnson et al. |
| 6,068,656 | A | 5/2000 | Von Oepen |
| 6,071,308 | A | 6/2000 | Ballou et al. |
| 6,077,880 | A | 6/2000 | Castillo et al. |
| 6,090,925 | A | 7/2000 | Woiszwillo et al. |
| 6,099,562 | A | 8/2000 | Ding et al. |
| 6,129,755 | A | 10/2000 | Mathis et al. |
| 6,143,037 | A | 11/2000 | Goldsten et al. |
| 6,143,314 | A | 11/2000 | Chandrashekar et al. |
| 6,146,356 | A | 11/2000 | Wang et al. |
| 6,146,404 | A | 11/2000 | Kim et al. |
| 6,147,135 | A | 11/2000 | Yuan et al. |
| 6,153,252 | A | 11/2000 | Hossainy et al. |
| 6,171,327 | B1 | 1/2001 | Daniel et al. |
| 6,190,699 | B1 | 2/2001 | Luzzi et al. |
| 6,193,744 | B1 | 2/2001 | Ehr et al. |
| 6,206,914 | B1 | 3/2001 | Soykan et al. |
| 6,217,608 | B1 | 4/2001 | Penn et al. |
| 6,231,599 | B1 | 5/2001 | Ley |
| 6,231,600 | B1 | 5/2001 | Zhong et al. |
| 6,245,104 | B1 | 6/2001 | Alt |
| 6,248,127 | B1 | 6/2001 | Shah et al. |
| 6,248,129 | B1 | 6/2001 | Froix |
| 6,251,980 | B1 | 6/2001 | Lan et al. |
| 6,268,053 | B1 | 7/2001 | Woiszwillo et al. |
| 6,273,913 | B1 | 8/2001 | Wright et al. |
| 6,284,758 | B1 | 9/2001 | Egi et al. |
| 6,299,635 | B1 | 10/2001 | Frantzen |
| 6,309,669 | B1 | 10/2001 | Setterstrom et al. |
| 6,319,541 | B1 | 11/2001 | Pletcher et al. |
| 6,325,821 | B1 | 12/2001 | Gaschino et al. |
| 6,336,934 | B1 | 1/2002 | Gilson et al. |
| 6,342,062 | B1 | 1/2002 | Suon et al. |
| 6,344,055 | B1 | 2/2002 | Shukov |
| 6,355,691 | B1 | 3/2002 | Goodman |
| 6,358,556 | B1 | 3/2002 | Ding et al. |
| 6,361,819 | B1 | 3/2002 | Tedeschi et al. |
| 6,362,718 | B1 | 3/2002 | Patrick et al. |
| 6,364,903 | B2 | 4/2002 | Tseng et al. |
| 6,368,658 | B1 | 4/2002 | Schwartz et al. |
| 6,372,246 | B1 | 4/2002 | Wei et al. |
| 6,387,121 | B1 | 5/2002 | Alt |
| 6,409,716 | B1 | 6/2002 | Sahatjian et al. |
| 6,414,050 | B1 | 7/2002 | Howdle et al. |
| 6,416,779 | B1 | 7/2002 | D-Augustine et al. |
| 6,448,315 | B1 | 9/2002 | Lidgren et al. |
| 6,458,387 | B1 | 10/2002 | Scott et al. |
| 6,461,380 | B1 | 10/2002 | Cox |
| 6,461,644 | B1 | 10/2002 | Jackson et al. |
| 6,488,703 | B1 | 12/2002 | Kveen et al. |
| 6,495,163 | B1 | 12/2002 | Jordan |
| 6,497,729 | B1 | 12/2002 | Moussy et al. |
| 6,506,213 | B1 | 1/2003 | Mandel et al. |
| 6,511,748 | B1 | 1/2003 | Barrows |
| 6,517,860 | B1 | 2/2003 | Rosser et al. |
| 6,521,258 | B1 | 2/2003 | Mandel et al. |
| 6,524,698 | B1 | 2/2003 | Schmoock |
| 6,530,951 | B1 | 3/2003 | Bates et al. |
| 6,537,310 | B1 | 3/2003 | Palmaz et al. |
| 6,541,033 | B1 | 4/2003 | Shah |
| 6,572,813 | B1 | 6/2003 | Zhang et al. |
| 6,602,281 | B1 | 8/2003 | Klein |
| 6,610,013 | B1 | 8/2003 | Fenster et al. |
| 6,627,246 | B2 | 9/2003 | Mehta et al. |
| 6,649,627 | B1 | 11/2003 | Cecchi et al. |
| 6,660,176 | B2 | 12/2003 | Tepper et al. |
| 6,669,785 | B2 | 12/2003 | DeYoung et al. |
| 6,669,980 | B2 | 12/2003 | Hanson et al. |
| 6,670,407 | B2 | 12/2003 | Howdle et al. |
| 6,682,757 | B1 | 1/2004 | Wright |
| 6,706,283 | B1 | 3/2004 | Appel et al. |
| 6,710,059 | B1 | 3/2004 | Labrie et al. |
| 6,720,003 | B2 | 4/2004 | Cheng et al. |
| 6,723,913 | B1 | 4/2004 | Barbetta |
| 6,726,712 | B1 | 4/2004 | Raeder-Devens et al. |
| 6,736,996 | B1 | 5/2004 | Carbonell et al. |
| 6,743,505 | B2 | 6/2004 | Antal et al. |
| 6,749,902 | B2 | 6/2004 | Yonker et al. |
| 6,755,871 | B2 | 6/2004 | Damaso et al. |
| 6,756,084 | B2 | 6/2004 | Fulton et al. |
| 6,767,558 | B2 | 7/2004 | Wang et al. |
| 6,780,475 | B2 | 8/2004 | Fulton et al. |
| 6,794,902 | B2 | 9/2004 | Becker et al. |
| 6,800,663 | B2 | 10/2004 | Asgarzadeh et al. |
| 6,815,218 | B1 | 11/2004 | Jacobsen et al. |
| 6,821,549 | B2 | 11/2004 | Jayaraman |
| 6,837,611 | B2 | 1/2005 | Kuo et al. |
| 6,838,089 | B1 | 1/2005 | Carlsson et al. |
| 6,838,528 | B2 | 1/2005 | Zhou |
| 6,858,598 | B1 | 2/2005 | McKearn et al. |
| 6,860,123 | B1 | 3/2005 | Uhlin et al. |
| 6,868,123 | B2 | 3/2005 | Bellas et al. |
| 6,884,377 | B1 | 4/2005 | Burnham et al. |
| 6,884,823 | B1 | 4/2005 | Plerick et al. |
| 6,897,205 | B2 | 5/2005 | Beckert et al. |
| 6,905,555 | B2 | 6/2005 | DeYoung et al. |
| 6,908,624 | B2 | 6/2005 | Hossainy et al. |
| 6,916,800 | B2 | 7/2005 | McKearn et al. |

(56) References Cited

U.S. PATENT DOCUMENTS

| | | |
|---|---|---|
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Rees et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,295,565 B2 | 10/2012 | Gu et al. |
| 8,298,565 B2 | 10/2012 | Taylor et al. |
| 8,333,803 B2 | 12/2012 | Park et al. |
| 8,377,356 B2 | 2/2013 | Huang et al. |
| 8,535,372 B1 | 9/2013 | Fox et al. |
| 8,597,716 B2 * | 12/2013 | Castro ............... A61F 2/915 |
| | | 427/2.21 |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 * | 6/2014 | Taylor ............... A61P 41/00 |
| | | 623/1.42 |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,090,029 B2 | 7/2015 | Prevost |
| 9,433,516 B2 | 9/2016 | McClain et al. |
| 9,474,833 B2 * | 10/2016 | Ruane ............... A61L 31/16 |
| 9,486,431 B2 | 11/2016 | McClain et al. |
| 9,510,976 B2 * | 12/2016 | Hossainy ............ A61B 1/06 |
| 9,511,554 B2 * | 12/2016 | Dave ............... A61L 29/126 |
| 9,592,141 B2 * | 3/2017 | Ramzi poor ............ A61F 2/954 |
| 9,668,894 B2 * | 6/2017 | Stankus ............ A61F 2/915 |
| 2001/0026804 A1 | 10/2001 | Boutignon |
| 2001/0034336 A1 | 10/2001 | Shah et al. |
| 2001/0037143 A1 | 11/2001 | Oepen |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworn et al. |
| 2002/0133072 A1 | 9/2002 | Wang et al. |
| 2002/0144757 A1 | 10/2002 | Craig et al. |
| 2002/0151959 A1 | 10/2002 | Von Oepen |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0209835 A1 | 11/2003 | Chun et al. |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0096477 A1 | 5/2004 | Chauhan et al. |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0148007 A1 | 7/2004 | Jackson et al. |
| 2004/0157789 A1 | 8/2004 | Geall |
| 2004/0170685 A1 | 9/2004 | Carpenter et al. |
| 2004/0181278 A1 | 9/2004 | Tseng et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0234748 A1 | 11/2004 | Stenzel |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0053639 A1 | 3/2005 | Shalaby |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070997 A1 | 3/2005 | Thornton et al. |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0101624 A1 * | 5/2005 | Betts ............... C07D 498/18 |
| | | 514/291 |
| 2005/0131513 A1 | 6/2005 | Myers et al. |
| 2005/0147734 A1 | 7/2005 | Seppala et al. |
| 2005/0159704 A1 | 7/2005 | Scott et al. |
| 2005/0166841 A1 | 8/2005 | Robida |

(56) References Cited

U.S. PATENT DOCUMENTS

| | | |
|---|---|---|
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0216075 A1 | 9/2005 | Wang et al. |
| 2005/0222676 A1 | 10/2005 | Shanley et al. |
| 2005/0238829 A1 | 10/2005 | Motherwell et al. |
| 2005/0245637 A1 | 11/2005 | Hossainy et al. |
| 2005/0255327 A1 | 11/2005 | Chaney |
| 2005/0260186 A1 | 11/2005 | Bookbinder et al. |
| 2005/0268573 A1 | 12/2005 | Maxfield et al. |
| 2005/0288481 A1 | 12/2005 | Desnoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0073329 A1* | 4/2006 | Boyce .................. D01F 6/605 428/364 |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026041 A1 | 2/2007 | DesNoyer et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1 | 9/2007 | Paul |
| 2007/0225795 A1* | 9/2007 | Granada .................. A61F 2/91 623/1.15 |
| 2007/0254012 A1* | 11/2007 | Ludwig .................. A61L 31/16 424/426 |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0091008 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0118544 A1 | 5/2008 | Wang |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2008/0300689 A1 | 12/2008 | Hossainy et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0076595 A1 | 3/2009 | Lindquist et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0137491 A1 | 6/2010 | Rose et al. |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1* | 9/2010 | McClain .................. A61L 31/10 623/1.42 |
| 2010/0256746 A1 | 10/2010 | Taylor et al. |
| 2010/0256748 A1 | 10/2010 | Taylor et al. |
| 2010/0262224 A1 | 10/2010 | Kleiner |

(56) References Cited

U.S. PATENT DOCUMENTS

| | | |
|---|---|---|
| 2010/0272775 A1 | 10/2010 | Cleek et al. |
| 2010/0272778 A1 | 10/2010 | McClain et al. |
| 2010/0285085 A1 | 11/2010 | Stankus et al. |
| 2010/0298928 A1 | 11/2010 | McClain et al. |
| 2010/0303881 A1 | 12/2010 | Hoke et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja |
| 2011/0172763 A1 | 7/2011 | Ndondo-Lay |
| 2011/0189299 A1 | 8/2011 | Okubo et al. |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0243884 A1* | 10/2011 | O'Shea ............ C07C 69/40 424/78.36 |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1* | 6/2012 | Shaw-Klein ............ A61F 2/88 623/1.15 |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1* | 9/2012 | Levi ............ A61P 31/00 424/400 |
| 2012/0239161 A1 | 9/2012 | Datta et al. |
| 2012/0271396 A1* | 10/2012 | Zheng ............ A61F 2/915 623/1.2 |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0084322 A1* | 4/2013 | Wu ............ A61L 27/46 424/426 |
| 2013/0084449 A1* | 4/2013 | Lewis ............ A61L 27/26 428/221 |
| 2013/0087270 A1 | 4/2013 | Hossainy et al. |
| 2013/0110138 A1* | 5/2013 | Hurtado ............ A61L 27/54 606/152 |
| 2013/0172853 A1 | 7/2013 | McClain et al. |
| 2013/0291476 A1 | 11/2013 | Broughton, Jr. et al. |
| 2014/0035192 A1* | 2/2014 | Ramzipoor ............ A61L 31/04 264/230 |
| 2014/0228932 A1* | 8/2014 | Rapoza ............ A61F 2/82 623/1.15 |
| 2014/0257465 A1* | 9/2014 | McClain ............ A61L 31/024 623/1.38 |
| 2014/0287134 A1* | 9/2014 | To ............ A61K 31/60 427/2.25 |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2015/0250926 A1 | 9/2015 | McClain et al. |
| 2016/0067071 A1* | 3/2016 | Jose ............ A61F 2/844 623/1.15 |
| 2016/0095726 A1* | 4/2016 | McClain ............ C08L 67/04 623/1.46 |
| 2018/0116837 A1* | 5/2018 | Ramzipoor ............ A61F 2/945 |

FOREIGN PATENT DOCUMENTS

| | | |
|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 | 1/2004 |
| CN | 1575860 A | 2/2005 |
| CN | 1649551 | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 | 6/1994 |
| EP | 800801 A1 | 10/1997 |
| EP | 0876806 A1 | 11/1998 |
| EP | 0982041 | 3/2000 |
| EP | 1195822 A2 | 4/2002 |
| EP | 1325758 A2 | 7/2003 |
| EP | 1327422 A1 | 7/2003 |
| EP | 1454677 | 9/2004 |
| EP | 1502655 A2 | 2/2005 |
| EP | 1750784 A1 | 2/2007 |
| EP | 1810665 A1 | 7/2007 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 1994-098902 | 4/1994 |
| JP | H06218063 A | 8/1994 |
| JP | H08206223 A | 8/1996 |
| JP | H09-056807 | 3/1997 |
| JP | H1029524 A | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2001521503 A | 11/2001 |
| JP | 2003-205037 | 7/2003 |
| JP | 2003-533286 | 11/2003 |
| JP | 2003-5339493 | 11/2003 |
| JP | 2003533492 | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2004528060 A | 9/2004 |
| JP | 2005-505318 | 2/2005 |
| JP | 2005519080 A | 6/2005 |
| JP | 2005-523119 | 8/2005 |
| JP | 2005-523332 | 8/2005 |
| JP | 2005-296690 | 10/2005 |
| JP | 2006506191 A | 2/2006 |
| JP | 2006512175 A | 4/2006 |
| JP | 2007502281 A | 2/2007 |
| JP | 2007215620 A | 8/2007 |
| JP | 2009-501566 | 1/2009 |
| JP | 2009529399 A | 8/2009 |
| JP | 2010052503 A | 3/2010 |
| JP | 2010515539 A | 5/2010 |
| JP | 2010516307 A | 5/2010 |
| JP | 2011517589 A | 6/2011 |
| JP | 2012527318 A | 11/2012 |
| KR | 10-2004-0034064 | 4/2004 |
| KR | 10-1231197 B1 | 2/2013 |
| WO | 9409010 A1 | 4/1994 |
| WO | WO-95/006487 | 3/1995 |
| WO | 9616691 A1 | 6/1996 |
| WO | WO-96/20698 | 7/1996 |
| WO | 9632907 A1 | 10/1996 |
| WO | 9641807 A1 | 12/1996 |
| WO | WO-97/045502 | 12/1997 |

(56) References Cited

FOREIGN PATENT DOCUMENTS

| | | |
|---|---|---|
| WO | 9802441 A2 | 1/1998 |
| WO | 9908729 A1 | 2/1999 |
| WO | 9915530 A1 | 4/1999 |
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 00032238 A1 | 6/2000 |
| WO | 0114387 A1 | 3/2001 |
| WO | WO-2001/054662 | 8/2001 |
| WO | 0187345 A1 | 11/2001 |
| WO | 0187368 A1 | 11/2001 |
| WO | WO-2001-087371 | 11/2001 |
| WO | WO-2001/087372 | 11/2001 |
| WO | 0226281 A1 | 4/2002 |
| WO | WO-2002/040702 | 5/2002 |
| WO | WO 2002/043799 | 6/2002 |
| WO | 02055122 A1 | 7/2002 |
| WO | WO-2002-074194 A2 | 9/2002 |
| WO | WO-2002/090085 | 11/2002 |
| WO | 02100456 A1 | 12/2002 |
| WO | WO-2003/039553 | 5/2003 |
| WO | WO-2003-082368 A | 10/2003 |
| WO | 03090684 A2 | 11/2003 |
| WO | WO-2003/101624 A1 | 12/2003 |
| WO | WO-2004/009145 | 1/2004 |
| WO | 2004028406 A1 | 4/2004 |
| WO | WO-2004/028589 | 4/2004 |
| WO | WO-2004/043506 | 5/2004 |
| WO | WO-2004/045450 | 6/2004 |
| WO | 2004101017 A2 | 11/2004 |
| WO | WO-2004/098574 | 11/2004 |
| WO | 2005018696 A1 | 3/2005 |
| WO | WO-2005/042623 A1 | 5/2005 |
| WO | WO-2005/063319 | 7/2005 |
| WO | WO-2005/069889 | 8/2005 |
| WO | WO-2005/117942 A2 | 12/2005 |
| WO | WO-2006/014534 | 2/2006 |
| WO | WO-2006/052575 | 5/2006 |
| WO | 2006063021 A2 | 6/2006 |
| WO | 2006063430 A1 | 6/2006 |
| WO | WO-2006/065685 | 6/2006 |
| WO | WO-2006/083796 A2 | 8/2006 |
| WO | WO-2006/099276 A2 | 9/2006 |
| WO | 2007017707 A2 | 1/2007 |
| WO | 2007017708 A3 | 1/2007 |
| WO | WO-2007-002238 | 1/2007 |
| WO | WO-2007/011707 A2 | 1/2007 |
| WO | WO-2007/011707 A3 | 1/2007 |
| WO | WO-2007/011708 A2 | 1/2007 |
| WO | WO-2007/011708 A3 | 1/2007 |
| WO | WO-2007/092179 | 8/2007 |
| WO | 2007106441 A2 | 9/2007 |
| WO | WO-2007/127363 A2 | 11/2007 |
| WO | WO 2007/143609 | 12/2007 |
| WO | 2008024626 A2 | 2/2008 |
| WO | WO-2008/042909 | 4/2008 |
| WO | WO-2008/046641 | 4/2008 |
| WO | WO-2008/046642 | 4/2008 |
| WO | WO-2008/052000 | 5/2008 |
| WO | WO-2008/070996 | 6/2008 |
| WO | WO-2008/086369 | 7/2008 |
| WO | WO 2008/131131 A1 | 10/2008 |
| WO | WO-2008/0148013 | 12/2008 |
| WO | 09039553 A1 | 4/2009 |
| WO | 09051614 A1 | 4/2009 |
| WO | WO-2009/051780 | 4/2009 |
| WO | 2009096822 A1 | 8/2009 |
| WO | 2009113605 A1 | 9/2009 |
| WO | 2009120361 A2 | 10/2009 |
| WO | WO-2009/0146209 | 12/2009 |
| WO | 2010001932 A1 | 1/2010 |
| WO | WO-2010/009335 | 1/2010 |
| WO | WO-2010/075590 | 7/2010 |
| WO | 2010086863 A2 | 8/2010 |
| WO | WO-2010/111196 A2 | 9/2010 |
| WO | WO-2010/111196 A3 | 9/2010 |
| WO | WO-2010/111232 A3 | 9/2010 |
| WO | WO-2010/111232 A9 | 9/2010 |
| WO | WO-2010/111238 A2 | 9/2010 |
| WO | WO-2010/111238 A3 | 9/2010 |
| WO | WO-2010/120552 A2 | 10/2010 |
| WO | WO-2010/120552 A3 | 10/2010 |
| WO | WO-2010/121187 A2 | 10/2010 |
| WO | WO-2010/121187 A3 | 10/2010 |
| WO | 2010135369 A1 | 11/2010 |
| WO | 10136604 A1 | 12/2010 |
| WO | WO-2011/009096 A1 | 1/2011 |
| WO | WO-2011/097103 | 8/2011 |
| WO | 2011119159 A1 | 9/2011 |
| WO | WO-2011/119762 | 9/2011 |
| WO | WO-2011/130448 | 10/2011 |
| WO | WO-2011/133655 | 10/2011 |
| WO | WO-2012/009684 | 1/2012 |
| WO | WO-2012/034079 | 3/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | 2013003644 A1 | 1/2013 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |
| WO | 2014165264 A1 | 10/2014 |
| WO | 2014186532 A1 | 11/2014 |
| WO | 2015181826 A1 | 12/2015 |

OTHER PUBLICATIONS

Akoh et al., "One-Stage Synthesis of Raffinose Fatty Acid Polyesters." Journal Food Science 52:1570 (1987).
Albert et al., "Antibiotics for preventing recurrent urinary tract infection in non-pregnant women," Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2006270221 Exam Report dated Apr. 6, 2010.
AU2007243268 Exam Report dated May 15, 2013.
AU2007243268 Exam Report dated Aug. 31, 2011.
AU2009251504 Exam Report dated Dec. 8, 2011.
AU2009270849 Exam Report dated Feb. 14, 2012.
AU2011232760 Exam Report dated Apr. 10, 2013.
AU2011256902 Exam Report dated Jun. 13, 2013.
AU2012203203 Exam Report dated Apr. 12, 2013.
AU2012203577 Exam Report dated Jun. 7, 2013.
AU2011256902 Office Action dated Jun. 10, 2014.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatment of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).

(56) References Cited

OTHER PUBLICATIONS

Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. Wiley and Sons, p. 1-24. (2007).
CA 2757276 Office Action dated Feb. 15, 2013.
CA 2757276 Office Action dated Feb. 5, 2014.
CA 2794704 Office action dated Feb. 7, 2014.
CA 2613280 Office Action dated Oct. 2, 2012.
CA 2615452 Office Action dated Dec. 19, 2012.
CA 2615452 Office Action dated Oct. 8, 2013.
CA 2650590 Office action dated Jul. 23, 2013.
CA 2613280 Office action dated Dec. 10, 2013.
CA 2667228 Office action dated Jan. 22, 2014.
CA 2679712 Office action dated Feb. 24, 2014.
CA 2684482 Office Action dated Nov. 10, 2011.
CA 2684482 Office Action dated Jul. 11, 2012.
CA 2688314 Office Action dated Jun. 6, 2012.
CA 2667228 office action dated May 7, 2013.
CA 2730995 Office action dated May 29, 2013.
CA 2730995 Office Action dated Sep. 26, 2012.
CA 2730995 Office Action dated Feb. 20, 2014.
CA 2756307 Office Action dated Feb. 18, 2013.
CA 2756307 Office Action dated Mar. 24,2014.
CA 2756386 Office Action dated Mar. 15, 2013.
CA 2756388 Office Action dated Apr. 11, 2013.
CA 2756388 Office Action dated Apr. 14, 2014.
CA 2759015 Office Action dated Apr. 8, 2013.
CA 2759015 Office Action dated Jul. 21, 2014.
CA 2756386 Office Action dated Oct. 24, 2013.
CA 2756386 Office Action dated May 16, 2014.
CA 2805631 Office Action dated Jan. 17, 2014.
CA 2823355 Office Action dated Apr. 14, 2014.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. 26(35):7418-24 (2005).
Chłopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334 (1984), pp. 337-355 (1984).
CN 2006800258093 Office Action dated May 30, 2012.
CN 200780047425.6 Office action dated Aug. 3, 2012.
CN 200780047425.6 Office Action dated Feb. 28, 2013.
CN 200880007308.1 Office Action dated Jul. 3, 2013.
CN 200880007308.1 Office Action dated Nov. 23, 2011.
CN 200880007308.1 Office Action dated Oct. 18, 2012.
CN 200880007308.1 Office Action dated Jan. 2, 2014.
CN 200880020515 Office Action dated Jul. 22, 2013.
CN 200880020515 Office Action dated Oct. 9, 2012.
CN 200880020515 Office Action dated Apr. 15, 2014.
CN 200880100102.3 Office Action dated Apr. 11, 2013.
CN 200880100102.3 Office Action dated Jun. 1, 2012.
CN 200880100102.3 Office Action dated Dec. 11, 2013.
CN 200880100102.3 Office Action dated Aug. 27, 2014.
CN 200980122691 Office Action dated Oct. 10, 2012.
CN 200980136432.2 Office Action dated Jan. 14, 2013.
CN 200980136432.2 Office Action dated Nov. 4, 2013.
CN 200980136432.2 Office Action dated Jul. 3, 2014.
CN 201080024973.9 Office Action dated Dec. 20, 2013.
CN 201080024973.9 Office Action dated Aug. 7, 2014.
Cohen, et al. "Sintering Technique for the Preparation of Polymer Matrices for the Controlled Release of Macromolecules." Journal of Pharamceutical Sciences, vol. 73, No. 8, p. 1034-1037 (1984).
Colombo et al. "Selection of Coronary Stents," Journal of the American College of Cardiology, vol. 40, No. 6, . p. 1021-1033 (2002).
CRC Handbook of chemistry and physics. 71st ed. David R. Lide, Editor-in-Chief. Boca Raton, FL, CRC Press; 6-140 (1990).
Cyrus et al., "Intramural delivery of rapamycin with alphavbeta3-targeted paramagnetic nanoparticles inhibits stenosis after balloon injury," Arterioscler Thromb Vasc Biol 28:820-826 (2008).
DERWENT-ACC-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides." J. Polym Sci. 25:3373-3386 (1987).
Domingo, C. et al., "Precipication of ultrafine organic crystals from the rapid expansion of supercritical solutions over a capillary and a frit nozzle," J. Supercritical Fluids 10:39-55 (1997).
Dzik-Jurasz, "Molecular imaging in vivo: an introduction," The British Journal of Radiology, 76:S98-S109 (2003).
EA 200901254 Office Action dated Jul. 29, 2013.
EA 200901254/28 Office Action dated Jun. 28, 2012.
EA 201001497 Office Action dated Feb. 11, 2013.
EA 201001497 Office Action dated Jul. 29, 2013.
Electrostatic Process, Wiley Encyclopedia of Electrical and Electronics Engineering, John Wiley & Sons, Inc. 7:15-39 (1999).
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Office Action dated Mar. 15, 2013.
EP06787258.0 Search Report dated Feb. 6, 2012.
EP07756094.4 Office Action dated Jan. 21, 2014.
EP07756094.4 Office Action dated May 29, 2013.
EP07756094.4 Search Report dated Aug. 31, 2012.
EP08705772.5 Office Action dated Oct. 30, 2013.
EP08705772.5 Search Report dated Feb. 20, 2013.
EP08733210.2 Office Action dated Jul. 16, 2013.
EP08733210.2 Search Report dated Oct. 23, 2012.
EP08756215.3 Search Report dated Oct. 5, 2011.
EP08756215.3 Search Report dated Jan. 28, 2013.
EP09755571.8 Office Action dated Dec. 13, 2013.
EP09755571.8 Search Report dated Apr. 9, 2013.
EP09798764.8 Search Report dated Sep. 30, 2013.
EP09805981.9 Office Action dated Feb. 13, 2013.
EP10756676.2 Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
EP10800642.0 Search Report dated Mar. 19, 2014.
EP11772624.0 Search Report dated Jun. 5, 2014.
EP09798764.8 Office Action dated Jun. 30, 2014.
Ettmayer et al. Lessons learned from marketed and investigational prodrugs. J Med Chem. 47(10):2393-404 (2004).
Fibbi et al., "Chronic inflammation in the pathogenesis of benign prostatic hyperplasia," Int J Androl. 33(3):475-88 (2010).
Fleischmann et al., "High Expression of Gastrin-Releasing Peptide Receptors in the Vascular bed of Urinary Tract Cancers: Promising Candidates for Vascular Targeting Applications." Endocr. Relat. Cancer 16(2):623-33 (2009).
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," NeuroReport 19(16):1585-1588 (2008).
Fulton et al. Thin Fluoropolymer films and nanoparticle coatings from the rapid expansion of supercritical carbon dioxide solutions with electrostatic collection, Polymer Communication. 2627-3632 (2003).

(56) References Cited

OTHER PUBLICATIONS

Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, Endothelium and Des Jun. 3, 2008:2123-9 (2008).
Han, et al., "Studies of a Novel Human Thrombomodulin Immobilized Substrate: Surface Characterization and Anticoagulation Activity Evaluation." J. Biomater. Sci. Polymer Edn, 12 (10), 1075-1089 (2001).
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 2933-2937 (2003).
Hinds, WC. Aerosol Technology, Properties, Behavior and Measurement of Airborne Particles, Department of Environmental Health Sciences, Harvard University School of Public Health, Boston, Massachusetts. 283-314 (1982).
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR—IR and FT-Raman Spectroscopy," J. of Structural Biology, 132, 112-122 (2000).
ID—W00201003529 Office Action dated Apr. 28, 2014.
IL—208648 Official Notification dated Feb. 9, 2012.
IL—201550 Official Notification dated Dec. 8, 2013.
IN-368/DELNP/2008 Exam Report dated Oct. 17, 2011.
IN-6884/DELNP/2009 Office Action dated Oct. 31, 2013.
IN-7740/DELNP/2009 Office Action dated Jul. 29, 2014.
Jackson et al., "Characterization of perivascular poly(lactic-co-glycolic acid) films containing paclitaxel" *Int. J. of Pharmaceutics*, 283:97-109 incorporated in its entirety herein by reference (2004).
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" *Biomacromolecules*. 7: 2483-2491 (2006).
Johns, H.E, J.R.Cunningham, Thomas, Charles C., Publisher, "The Physics of Radiology," Springfield, IL, pp. 133-143 (1983).
Joner et al. "Site-specific targeting of nanoparticle prednisolone reduces in-stent restenosis in a rabbit model of established atheroma," Arterioscler Thromb Vasc Biol. 28:1960-1966 (2008).
Jovanovic et al. "Stabilization of Proteins in Dry Powder Formulations Using Supercritical Fluid Technology," Pharm. Res. 21(11) (2004).
JP 2008-521633 Office Action dated Oct. 12, 2012.
JP2008-521633 Office Action dated Dec. 28, 2011.
JP-2009-534823 Office Action dated Apr. 23, 2013.
JP-2009-534823 Office Action dated Feb. 21, 2012.
JP-2009-534823 Office Action dated Sep. 20, 2012.
JP-2009-545647 Office Action dated Jun. 5, 2012.
JP-2009-545647 Office Action dated May 14, 2013.
JP-2009-545647 Office Action dated Apr. 22, 2014.
JP-2010-504253 Office Action dated Dec. 12, 2011.
JP-2010-504253 Office Action dated Dec. 7, 2012.
JP-2010-510441 Office action dated May 7, 2013.
JP-2011-505248 Office action dated Jun. 4, 2013.
JP-2011-518920 Office action dated Dec. 17, 2012.
JP-2011-518920 Office action dated Oct. 23, 2013.
JP-2012-503677 Office action dated Jan. 18, 2013.
JP-2012-503677 Office action dated Nov. 1, 2013.
JP-2012-151964 Office Action dated Dec. 10, 2013.
JP-2013-024508 Office Action dated May 2, 2014.
JP-2013-190903 Office Action dated Sep. 2, 2014.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Chemistry and the new uses of Sucrose: How Important?" Pur and Appl. Chem 56:833-844 (1984).
Khan et al., "Cyclic Acetals of 4,1',6'-Trichloro-4,1',6',-Trideoxy-Trideoxy-galacto-Sucrose and their Conversion into Methyl Ether Derivatives." Carb. Res. 198:275-283 (1990).
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters 34:7767 (1933).
Khayankarn et al., "Adhesion and Permeability of Polyimide-Clay Nanocomposite Films for Protective Coatings," Journal of Applied Polymer Science, vol. 89, 2875-2881 (2003).
Koh et al., A novel nanostructured poly(lactic-co-glycolic-acid)—multi-walled carbon nanotube composite for blood-contacting applications: Thrombogenicity studies, Acta Biomaterialia 5:3411-3422 (2009).
KR10-2008-7003756 Office Action dated Sep. 23, 2013.
KR10-2008-7003756 Office Action dated Oct. 30, 2012.
KR10-2013-7031237 Office Action dated Mar. 17, 2014.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, 1229-1234 (1998).
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Pediatr Drugs 3(7):481-494 (2001).
Mahoney et al., "Three-Dimensional Compositional Analysis of Drug Eluting Stent Coatings Using Cluster Secondary Ion mass Spectrometry," Anal. Chem., 80, 624-632 (2008).
Mario, C.D. et al., "Drug-Eluting Bioabsorbable Magnesium Stent," J. Interventional Cardiology 16(6):391-395 (2004).
Matsumoto, D, et al. Neointimal Coverage of Sirolimus-Eluting Stents at 6-month Follow-up: Evaluated by Optical Coherence Tomography, European Heart Journal, 28:961-967 (2006).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Mei et al., "Local Delivery of Modified Paclitaxel-Loaded Poly( ε-caprolactone)/Pluronic F68 Nanoparticles for Long-Term Inhibition of Hyperplasia," Journal of Pharmaceutical Sciences, vol. 98, No. 6, Jun. 2009.

(56) References Cited

OTHER PUBLICATIONS

Melonakos et al., Treatment of low-grade bulbar transitional cell carcinoma with urethral instillation of mitomycin C, Adv. Urol., 173694 Epub; (2008).
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Merriam-Webster Online Dictionary, obtained online at: http://www.merriam-webster.com/dictionary/derivative, downloaded Jan. 23, 2013.
Middleton and Tipton, Synthetic biodegradable polymers as orthopedic devises. Biomaterials 21:2335-46 (2000).
Minchin, "Nanomedicine: sizing up targets with nanoparticles," Nature Nanotechnology, vol. 33, 12-13 (2008).
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 46(4):857-65 (2000).
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
MX/a/2010/01148 Office Action dated Feb. 11, 2014.
NZ 588549 Examination Report dated Mar. 28, 2011.
NZ 600814 Examination Report dated Jun. 29, 2012.
O'Neil et al., "Extracellular matrix binding mixed micelles for drug delivery applications," Journal of Controlled Release 137:146-151 (2009).
O'Donnell et al., "Salvage intravesical therapy with interferon-alpha 2b plus low dose bacillus Calmette-Guerin alone perviously failed," Journ. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647-658 (2005).
PCT/US06/24221 International Preliminary Report on Patentability dated Dec. 24, 2007.
PCT/US06/24221 International Search Report dated Jan. 29, 2007.
PCT/US06/27321 International Preliminary Report on Patentability dated Jan. 16, 2008.
PCT/US06/27321 International Search Report dated Oct. 16, 2007.
PCT/US06/27322 International Preliminary Report on Patentability dated Jan. 16, 2008.
PCT/US06/27322 International Search Report dated Apr. 25, 2007.
PCT/US07/10227 International Preliminary Report on Patentability dated Oct. 28, 2008.
PCT/US07/10227 International Search Report dated Aug. 8, 2008.
PCT/US07/80213 International Preliminary Report on Patentability dated Apr. 7, 2009.
PCT/US07/80213 International Search Report dated Apr. 16, 2008.
PCT/US07/82275 International Search Report dated Apr. 18, 2008.
PCT/US07/82775 International Preliminary Report on Patentablity dated Apr. 28,2009.
PCT/US08/11852 International Preliminary Report on Patentability dated Apr. 20, 2010.
PCT/US08/11852 International Search Report dated Dec. 19, 2008.
PCT/US08/50536 International Preliminary Report on Patentability dated Jul. 14, 2009.
PCT/US08/50536 International Search Report dated Jun. 2, 2008.
PCT/US08/60671 International Preliminary Report on Patentability dated Oct. 20, 2009.
PCT/US08/60671 International Search Report dated Sep. 5, 2008.
PCT/US08/64732 International Preliminary Report on Patentability dated Dec. 1, 2009.
PCT/US08/64732 International Search Report dated Sep. 4, 2008.
PCT/US09/41045 International Preliminary Report on Patentability dated Oct. 19, 2010.
PCT/US09/41045 International Search Report dated Aug. 11, 2009.
PCT/US09/50883 International Preliminary Report on Patentability dated Jan. 18, 2011.
PCT/US09/50883 International Search Report dated Nov. 17, 2009.
PCT/US09/69603 International Preliminary Report on Patentability dated Jun. 29, 2011.
PCT/US09/69603 International Search Report dated Nov. 5, 2010.
PCT/US10/28195 International Preliminary Report on Patentability dated Sep. 27, 2011.
PCT/US10/28195 Search Report and Written Opinion dated Jan. 21, 2011.
PCT/US10/28253 International Preliminary Report on Patentability dated Sep. 27, 2011.
PCT/US10/28253 Search Report and Written Opinion dated Dec. 6, 2010.
PCT/US10/28265 International Report on Patentability dated Sep. 27, 2011.
PCT/US10/28265 Search Report and Written Opinion dated Dec. 3, 2010.
PCT/US10/29494 International Preliminary Report on Patentability dated Oct. 4, 2011.
PCT/US10/29494 Search Report and Written Opinion dated Feb. 7, 2011.
PCT/US10/31470 International Preliminary Report on Patentability dated Oct. 18, 2011.
PCT/US10/31470 Search Report and Written Opinion dated Jan. 28, 2011.
PCT/US10/42355 International Preliminary Report on Patentability dated Jan. 17, 2012.
PCT/US10/42355 Search Report dated Sep. 2, 2010.
PCT/US11/032371 International Report on Patentability dated Oct. 16, 2012.
PCT/US11/032371 International Search Report dated Jul. 7, 2011.
PCT/US11/044263 International Search Report, International Preliminary Report on Patentability and Written Opinion dated Feb. 9, 2012.
PCT/US11/051092 International Preliminary Report on Patentability dated Mar. 21, 2013.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/22623 Search Report and Written Opinion dated Mar. 28, 2011.
PCT/US11/29667 International Search Report and Written Opinion dated Jun. 1, 2011.
PCT/US11/67921 International Preliminary Report on Patentability dated Jul. 11, 2013.
PCT/US11/67921 Search Report and Written Opinion dated Jun. 22, 2012.
PCT/US12/040040 International Search Report dated Sep. 7, 2012.
PCT/US12/33367 International Preliminary Report on Patentability dated Oct. 15, 2013.
PCT/US12/33367 International Search Report dated Aug. 1, 2012.
PCT/US12/46545 International Search Report dated Nov. 20, 2012.
PCT/US13/41466 International Search Report and Written Opinion dated Oct. 17, 2013.

(56) References Cited

OTHER PUBLICATIONS

PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
PCT/US2014/025017 International Search Report and Written Opinion dated Jul. 7, 2014.
Perry et al., Chemical Engineers Handbook, 5th Edition, McGraw-Hill, New York, 20-106 (1973).
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 9:1-9.97 (2001).
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Putkisto, K. et al. "Polymer Coating of Paper Using Dry Surface Treatment—Coating Structure and Performance", ePlace newsletter, vol. 1, No. 8, pp. 1-20 (2004).
Raganath et al., "Hydrogel matrix entrapping PLGA-paclitaxel microspheres: drug delivery with near zero-order release and implantability advantages for malignant brain tumour," Pharm Res (Epub) Jun. 20, 2009.
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 1;209-216 (2008).
Ristikankare et al., "Sedation, topical pharnygeal anesthesia and cardiorespiratory safety during gastroscopy," J. Clin Gastorenterol. 40(1):899-905 (2006).
Sahajanand Medical Technologies (Supralimus Core; Jul. 6, 2008).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons vol. 20 pp. 726-736 (1982).
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S0022836999925901.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems—An Experimental Approach," Biomed Techn 47, Erg. 1, S. 124-126 (2002).
Schreiber, S.L. et al., "Atomic Structure of the Rapamycin Human Immunophilin FKBP-12 Complex," J. Am. Chem. Soc. 113:7433-7435 (1991).

Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., vol. 344, No. 15, pp. 1117-1124 (2001).
SG201007602-4 Examination Report dated Feb. 13, 2013.
SG201007602-4 Written Opinion dated May 25, 2012.
Shekunov et al. "Crystallization Processes in Pharmaceutical Technology and Drug Delivery Design." Journal of Crystal Growth 211, pp. 122-136 (2000).
Simpson et al., "Hyaluronan and hyaluronidase in genitourinary tumors." Front Biosci. 13:5664-5680 (2009).
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Szabadits et al., "Flexibility and trackability of laser cut coronary stent systems," Acta of Bioengineering and Biomechanics 11(3):11-18 (2009).
Testa, B. Prodrug research: futile or fertile? Biochem Pharmacol. 68(11):2097-106 (2004).
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Torchlin, "Micellar Nanocarriers: Pharmaecutial Perspectives," Pharmaceutical Research, vol. 24, No. 1, Jan. 2007.
U.S. Appl. No. 11/158,724 Office Action dated Dec. 31, 2013.
U.S. Appl. No. 11/158,724 Office Action dated May 23, 2013.
U.S. Appl. No. 11/158,724 Office Action dated Sep. 17, 2009.
U.S. Appl. No. 11/158,724 Office Action dated Sep. 26, 2012.
U.S. Appl. No. 11/158,724 Office Action dated Sep. 8, 2008.
U.S. Appl. No. 11/158,724 Office Action dated Jun. 25, 2014.
U.S. Appl. No. 11/877,591 Final Action dated Nov. 4, 2013.
U.S. Appl. No. 11/877,591 Office Action dated Feb. 29, 2012.
U.S. Appl. No. 11/877,591 Office Action dated Jul. 1, 2013.
U.S. Appl. No. 11/877,591 Office Action dated Sep. 21, 2012.
U.S. Appl. No. 11/877,591 Office Action dated May 7, 2014.
U.S. Appl. No. 11/995,685 Office Action dated Aug. 20, 2010.
U.S. Appl. No. 11/995,685 Office Action dated Nov. 24, 2009.
U.S. Appl. No. 11/995,687 Office Action dated Apr. 6, 2012.
U.S. Appl. No. 11/995,687 Office Action dated Sep. 28, 2011.
U.S. Appl. No. 12/298,459 Office Action dated Apr. 6, 2012.
U.S. Appl. No. 12/298,459 Office Action dated Aug. 10, 2011.
U.S. Appl. No. 12/298,459 Office Action dated May 31, 2013.
U.S. Appl. No. 12/426,198 Office Action dated Feb. 6, 2012.
U.S. Appl. No. 12/426,198 Office Action dated Feb. 7, 2014.
U.S. Appl. No. 12/426,198 Office Action dated Mar. 23, 2011.
U.S. Appl. No. 12/443,959 Office Action dated Dec. 13, 2012.
U.S. Appl. No. 12/443,959 Office Action dated Feb. 15, 2012.
U.S. Appl. No. 12/504,597 Final Office Action dated Oct. 3, 2012.
U.S. Appl. No. 12/504,597 Office Action dated Apr. 1, 2014.
U.S. Appl. No. 12/504,597 Office Action dated Dec. 5, 2011.
U.S. Appl. No. 12/522,379 Office Action dated Apr. 8, 2014.
U.S. Appl. No. 12/522,379 Final Office Action dated Aug. 28, 2013.
U.S. Appl. No. 12/522,379 Office Action dated Dec. 26, 2012.
U.S. Appl. No. 12/595,848 Office Action dated Jan. 13, 2012.
U.S. Appl. No. 12/595,848 Office Action dated Mar. 15, 2013.
U.S. Appl. No. 12/595,848 Office Action dated Oct. 22, 2013.
U.S. Appl. No. 12/595,848 Office Action dated Jun. 3, 2014.
U.S. Appl. No. 12/601,101 Office Action dated Dec. 27, 2012.
U.S. Appl. No. 12/601,101 Office Action dated Feb. 13, 2014.
U.S. Appl. No. 12/601,101 Office Action dated Mar. 27, 2012.
U.S. Appl. No. 12/601,101 Office Action dated May 22, 2013.
U.S. Appl. No. 12/648,106 Final Office Action dated Sep. 25, 2012.
U.S. Appl. No. 12/648,106 Office Action dated Jan. 30, 2012.
U.S. Appl. No. 12/648,106 Office Action dated Sep. 18, 2013.
U.S. Appl. No. 12/729,156 Final Office Action dated Oct. 16, 2012.
U.S. Appl. No. 12/729,156 Office Action dated Feb. 1, 2012.

(56) References Cited

OTHER PUBLICATIONS

U.S. Appl. No. 12/729,156 Office Action dated Feb. 13, 2014.
U.S. Appl. No. 12/729,156 Office Action dated May 8, 2013.
U.S. Appl. No. 12/729,580 Final Action dated Nov. 14, 2013.
U.S. Appl. No. 12/729,580 Office Action dated Apr. 10, 2012.
U.S. Appl. No. 12/729,580 Office Action dated Jan. 22, 2013.
U.S. Appl. No. 12/729,580 Office Action dated Sep. 10, 2014.
U.S. Appl. No. 12/729,603 Final Office Action dated Oct. 10, 2012.
U.S. Appl. No. 12/729,603 Office Action dated Mar. 27, 2012.
U.S. Appl. No. 12/729,603 Office Action dated Jun. 25, 2014.
U.S. Appl. No. 12/738,411 Final Office Action dated Apr. 11, 2013.
U.S. Appl. No. 12/738,411 Office Action dated Aug. 21, 2013.
U.S. Appl. No. 12/738,411 Office Action dated Feb. 6, 2014.
U.S. Appl. No. 12/738,411 Office Action dated May 30, 2014.
U.S. Appl. No. 12/748,134 Office Action dated Jul. 18, 2013.
U.S. Appl. No. 12/751,902 Office Action dated Dec. 19, 2013.
U.S. Appl. No. 12/751,902 Office Action dated Jul. 13, 2012.
U.S. Appl. No. 12/762,007 Final Office Action dated Oct. 22, 2013.
U.S. Appl. No. 12/762,007 Final Office Action dated Apr. 30, 2014.
U.S. Appl. No. 12/762,007 Office action dated Feb. 11, 2013.
U.S. Appl. No. 13/014,632 Office action dated Jan. 10, 2014.
U.S. Appl. No. 13/014,632 Office action dated May 8, 2013.
U.S. Appl. No. 13/086,335 Office action dated May 22, 2013.
U.S. Appl. No. 13/086,335 Office action dated Apr. 4, 2014.
U.S. Appl. No. 13/229,473 Office Action dated Jun. 17, 2013.
U.S. Appl. No. 13/340,472 Office action dated Apr. 26, 2013.
U.S. Appl. No. 13/340,472 Office action dated Jan. 15, 2014.
U.S. Appl. No. 13/340,472 Office action dated Aug. 29, 2014.
U.S. Appl. No. 13/384,216 Final Action dated Nov. 6, 2013.
U.S. Appl. No. 13/384,216 Office action dated Apr. 24, 2013.
U.S. Appl. No. 13/605,904 Office Action dated Jun. 28, 2013.
U.S. Appl. No. 13/605,904 Office Action dated Nov. 27, 2012.
U.S. Appl. No. 13/445,723 Office action dated Mar. 14, 2014.
U.S. Appl. No. 13/090,525 Office action dated Apr. 11, 2014.
U.S. Appl. No. 11/995,685 Office Action dated Jun. 18, 2014.
Unger et al., "Poly(ethylene carbonate): A thermoelastic and biodegradable biomaterial for drug eluting stent coatings?" Journal of Controlled Release, vol. 117, Issue 3, 312-321 (2007).
Verma et al., "Effect of surface properties on nanoparticle-cell interactions," Small 6(1):12-21 (2010).
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 27:5588-95 (2000).
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. 11(7-8):348-54 (2006).
Witjes et al., "Intravesical pharmacotherapy for non-muscle-invasive bladder cancer: a critical analysis of currently available drugs, treatment schedules, and long-term results," Eur. Urol. 53(1):45-52 (2008).
Wu et al., "Study on the preparation and characterization of biodegradable polylactide/multi-walled carbon nanotubes nanocomposites." Polymer 48:4449-4458 (2007).
Xu et al., "Biodegradation of poly(l-lactide-co-glycolide tube stents in bile" Polymer Degradation and Stability. 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).

Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 91:1848-56. (2004).
Zilberman et al., Drug-Eluting bioresorbable stents for various applications, Annu Rev Biomed Eng., 8:158-180 (2006).
David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.
Analytical Ultracentrifugation of Polymers and Nanoparticles, W. Machtle and L. Borger, (Springer) 2006, p. 41.
Chalmers, et al. (2007) Wiley and Sons.
European International Search Report of PCT/EP01/05736 dated Oct. 24, 2001.
Finn et al. Differential Response of Delayed Healing . . . Circulation vol. 112 (2005) 270-8.
Greco et al. (Journal of Thermal Analysis and Calorimetry, vol. 72 (2003) 1167-1174.).
Handschumacher, R.E. et al., Purine and Pyrimidine Antimetabolites, Chemotherapeutic Agents, pp. 712-732, Ch. XV1-2, 3rd Edition, Edited by J. Holland, et al., Lea and Febigol, publishers.
Higuchi, Rate of Release of Medicaments from Ointment Bases Containing Drugs in Suspension, Journal of Pharmaceutical Sciences, vol. 50, No. 10, p. 874, Oct. 1961.
Ji, et al., "96-Wellliquid-liquid extraction liquid chromatographytandem mass spectrometry method for the quantitative determination of ABT-578 in human blood samples" Journal of Chromatography B. 805:67-75 (2004).
Ju et al., J. Pharm. Sci. vol. 84, No. 12, 1455-1463.
Levit, et al., "Supercritical CO2 Assisted Electrospinning" J. of Supercritical Fluids, 329-333, vol. 31, Issue 3, (Nov. 2004).
Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990).
Luzzi, L.A., J. Phann. Psy. 59:1367 (1970).
Park et al., Pharm. Res. (1987) 4(6):457-464.
PCT/EP01/05736 International Preliminary Examination Report dated Jan. 14, 2002.
PCT/EP2000/004658 International Search Report dated Sep. 15, 2000.
PCT/US06/27321 Written Opinion dated Oct. 16, 2007.
PCT/US11/33225 International Search Report and Written Opinion dated Jul. 7, 2011.
PCT/US12/50408 International Search Report dated Oct. 16, 2012.
PCT/US13/41466 International Preliminary Report on Patentability dated Nov. 18, 2014.
PCT/US13/42093 International Preliminary Report on Patentability dated Nov. 25, 2014.
PCT/US14/38117 International Search Report and Written Opinion dated Oct. 7, 2014.
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
Extended European Search Report for Application No. 14797966.0 dated Dec. 19, 2016.
Search Report from Singapore Application No. 2013054127 dated Jul. 26, 2017, 5 pages.
Datenblatt NIRflex® der Firma Medinol, NIRFlex TM Premounted Coronary Stent System, Instructions for Use, Medinol Ingenuity for Life, Doc #912000012 Draft F, Oct. 8, 2003, 18 pages.
Stoeckel et al., "A survey of stent designs", Minimally Invasive Therapy & Allied Technologies, Jan. 2002, 11 (4), Seite 137-147.
Wenda C. Carlyle et al: "Enhanced drug delivery capabilities from stents coated with absorbable polymer and crystalline drug", Journal of Controlled Release, vol. 162, No. 3, Sep. 1, 2012 (Sep. 1, 2012 ), pp. 561-567, XP055289527.
"Guidance for Industry / Coronary Drug-Eluting Stents Nonclinical and Clinical Studies", U.S. Department of Health and Human Services Food Drug Adminstration Center for Devices and Radio-

(56) References Cited

OTHER PUBLICATIONS logical Health (CDRH), Center for Drug-Evaluation and Research (CDER), Mar. 2008, <https://www.fda.gov/media/71521/download>, 89 pages.

Balakrishnan, Brinda, et al. "Intravascular drug release kinetics dictate arterial drug deposition, retention, and distribution." Journal of Controlled Release 123.2, Nov. 6, 2007, pp. 100-108.

Choi, Jiyeon, et al. "Effect of solvent on drug release and a spray-coated matrix of a sirolimus-eluting stent coated with poly (lactic-co-glycolic acid)." Langmuir 30.33, Publication dated Aug. 4, 2014, pp. 10098-10106.

Medinol Ingenuity for Life, "X-Suit NIR / Bilinary Metallic Stent", Copyright 2017, <https://www.medinol.com/us/products/x-suit-nir/>, 5 pages.

Medtronic, "EverFlex Self-expanding Peripheral Stent / Vascular Stenting", last updated Nov. 2017, <https://www.medtronic.com/us-en/healthcareprofessionals/products/cardiovascular/peripheral-biliary-stents/everflex.html>, 6 pages.

Medtronic, "Indications, Safety, and Warnings / IntraStent DoubleStrut LD Biliary Stents", <https://www.medtronic.com/us-en/healthcareprofessionals/products/cardiovascular/peripheral-biliary-stents/intrastentdoublestrut-ld-biliarv-stent/indicationssafety-warnings.html>, last updated Nov. 2017, 2 pages.

Medtronic, "IntraStent DoubleStrut LD Biliary Stents", last updated Nov. 2017, <https://www.medtronic.com/us-en/healthcareprofessionals/products/cardiovascular/peripheral-biliary-stents/intrastentdoublestrut-ld-biliary-stent.html>, 4 pages.

Minami, Yoshiyasu et al., "Endothelial dysfunction following drug-eluting stent implantation: a systematic review of the literature. International Journal of Cardiology", 165(2), May 10, 2013, pp. 222-228.

Stent: Medline Plus Medical Encyclopedia, National Institutes of Health / U.S. National Library of Medicine, last updated Mar. 23, 2020 <https://medlineplus.gov/ency/article/002303.htm>, 4 pages.

U.S. Department of Health and Human Services Food and Drug Administration Center for Devices and Radiological Health, "Metal Expandable Biliary Stents—Premarket Notificarion (510(k)) Submissions / Guidance for Industry and Food and Drug Administration Staff", Document issued on Jul. 27, 2019, <https://www.fda.gov/media/72693/download>, 27 pages.

\* cited by examiner

BIOABSORBABLE BIOMEDICAL IMPLANTS

CROSS-REFERENCE TO RELATED APPLICATIONS

This application claims the benefit of U.S. Provisional Application No. 61/777,230, filed Mar. 12, 2013, which application is incorporated herein by reference.

BACKGROUND

The present disclosure relates to bioabsorbable stents made of polymeric materials and method of manufacturing the bioabsorbable stents.

SUMMARY OF THE DISCLOSURE

According to one aspect of the present disclosure, a biomedical implant is disclosed as including a tubular scaffold comprising a plurality of interconnected polymer struts. The interconnected polymer struts defines a plurality of deformable cells. The polymer struts have an average thickness of no more than 120 µm.

In one embodiment, the tubular scaffold maintains at least 50% of its nominal luminal cross sectional area under a pressure load of 50 mmHg. In another embodiment, the tubular scaffold maintains at least 80% of its nominal luminal cross sectional area under a pressure load of 50 mmHg.

In one embodiment, the tubular scaffold maintains at least 50% of its nominal luminal cross sectional area under a pressure load of 50 mmHg upon 3 months of exposure to saline in vitro. In another embodiment, the tubular scaffold maintains at least 50% of its deployed luminal cross sectional area under a pressure load of 50 mmHg upon 3 months in vivo.

In one embodiment, the tubular scaffold maintains at least 50% of its nominal luminal cross sectional area under a pressure load of 50 mmHg upon 6 months of exposure to saline in vitro. In another embodiment, the tubular scaffold maintains at least 50% of its nominal luminal cross sectional area under a pressure load of 50 mmHg upon 6 months in vivo.

In one embodiment, at least 80% of the polymer struts are bioabsorbed within 2 years after deployment in vivo. In another embodiment, at least 80% of the polymer struts are bioabsorbed within 1 year after deployment in vivo.

In one embodiment, the polymer struts have an average thickness of no more than 100 µm. In another embodiment, the polymer struts have an average thickness of no more than 80 µm.

In one embodiment, the polymer struts have anisotropic elastic modulus. In a refinement, the polymer struts have an average longitudinal (i.e. along the axis of the polymer struts) elastic modulus and an average lateral elastic modulus, the average longitudinal elastic modulus being greater than the average lateral elastic modulus. In a further refinement, the average longitudinal elastic modulus is at least three times the average lateral elastic modulus. In another further refinement, the average longitudinal elastic modulus is at least five times the average lateral elastic modulus. In yet another further refinement, the average longitudinal elastic modulus is at least ten times the average lateral elastic modulus.

In one embodiment, the polymer struts include polymer chains that are longitudinally (i.e. along the axis of the polymer struts) aligned. In one embodiment, the polymer struts include crystalline domains, in which the polymer chains are longitudinally aligned. In another embodiment, more than 50% of polymer chains in the polymer struts are longitudinally aligned. In another embodiment, more than 70% of the polymer chains in the polymer struts are longitudinally aligned. In another embodiment, more than 90% of the polymer chains in the polymer struts are longitudinally aligned.

In one embodiment, the polymer struts have an average deformation angle of at least 60 degrees. In another embodiment, the polymer struts have an average deformation angle of at least 45 degrees.

In one embodiment, the polymer struts comprises a gel-spun polymer material. In a refinement, the polymer struts are not structurally reinforced with a metal material. In a further refinement, the gel-spun polymer material is selected from the group consisting of polylactides (PLA); poly (lactide-co-glycolide) (PLGA); polyanhydrides; polyorthoesters; poly(N-(2-hydroxypropyl) methacrylamide); poly(dl-lactide) (DLPLA); poly(l-lactide) (LPLA); poly(d-lactide) (DPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), poly(lactic acid-co-caprolactone) (PLACL), and mixtures or co-polymers thereof.

In one refinement, the gel-spun polymer material is PLGA. In a further refinement, the PLGA has a ratio of lactic acid monomer to glycolic acid monomer ranging from 72:28 to 78:22. In another further refinement, the PLGA has a ratio of lactic acid monomer to glycolic acid monomer ranging from 62:38 to 68:32. In another further refinement, the PLGA has a ratio of lactic acid monomer to glycolic acid monomer ranging from 47:53 to 53:47. In another further refinement, the PLGA has a weight average molecular weight of about 8,000 Dalton to about 12,000 Dalton. In another further refinement, the PLGA has a weight average molecular weight of about 12,000 Dalton to about 16,000 Dalton. In another further refinement, the PLGA has a weight average molecular weight of up to about 90,000 Dalton. In another refinement, the gel-spun polymer material is PLA or LPLA. In another refinement, the gel-spun polymer material is PGA. In some embodiment, the gel spun polymer material (e.g. PLGA, LPLA, PLA, PGA) has a weight average molecular weight of at least 90,000 Dalton, and optionally at least 100,000 Dalton.

In one embodiment, the polymer struts comprises a liquid crystalline polymer material. In a refinement, the liquid crystalline polymer material is drawn from a liquid crystalline melt or solution. In another refinement, the polymer struts are not structurally reinforced with a metal material. In a further refinement, the liquid crystalline polymer material is selected from the group consisting of polylactides (PLA); poly(dl-lactide) (DLPLA); poly(l-lactide) (LPLA); poly(d-lactide) (DPLA); polyglycolide (PGA); poly(dioxanone) (PDO); poly(l-lactide-co-glycolide) (PGA-LPLA); poly(l-lactide-co-dl-lactide) (LPLA-DLPLA), poly(lactic acid-co-caprolactone) (PLACL), and mixtures or co-polymers thereof.

In another refinement, the liquid crystalline polymer material has a crystallinity of at least 30%. In another refinement, the liquid crystalline polymer material has a crystallinity of at least 35%. In another refinement, the liquid crystalline polymer material has a crystallinity of at least 40%.

In another refinement, the liquid crystalline polymer material is PLA or LPLA. In another refinement, the liquid crystalline polymer material is PGA. In some embodiment, the liquid crystalline polymer material (e.g. LPLA, PLA, PGA) has a weight average molecular weight of at least 90,000 Dalton, and optionally at least 100,000 Dalton.

In one embodiment, the polymer struts include a polymer material selected from the group consisting of polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof.

In one embodiment, the tubular scaffold is expandable from an undeployed diameter to a nominal diameter without affecting the structural integrity of the tubular scaffold. In a refinement, the tubular scaffold is further expandable from the nominal diameter to an over-deployed diameter without affecting the structural integrity of the tubular scaffold. In a further refinement, the over-deployed diameter is about 1.0 mm greater than the nominal diameter. In another further refinement, the over-deployed diameter is about 0.5 mm greater than the nominal diameter.

In one refinement, the tubular scaffold is expandable by an inflatable balloon positioned within the tubular scaffold. In a further refinement, the tubular scaffold has a nominal diameter of 2.25 mm at nominal balloon pressure. In another further refinement, the tubular scaffold has a nominal diameter of 2.5 mm at nominal balloon pressure. In another further refinement, the tubular scaffold has a nominal diameter of 3.0 mm at nominal balloon pressure. In another further refinement, the tubular scaffold has a nominal diameter of 3.5 mm at nominal balloon pressure. In another further refinement, the tubular scaffold has a nominal diameter of 4.0 mm at nominal balloon pressure. In another further refinement, the tubular scaffold has a nominal diameter of 4.5 mm at nominal balloon pressure.

In one refinement, the polymer struts comprise a shape-memory polymer and wherein tubular scaffold is self-expandable. In a further refinement, the tubular scaffold is self-expandable upon change in temperature. In another further refinement, the tubular scaffold is self-expandable upon change in crystallinity of the shape-memory polymer.

In one embodiment, the tubular scaffold is formed from a plurality of sinusoidal polymer fibers. In a refinement, the sinusoidal polymer fibers are interconnected at a plurality of connecting points.

In one embodiment, the tubular scaffold is formed from a single polymer fiber. In a refinement, the single polymer fiber comprises a plurality of sinusoidal sections interconnected at a plurality of connecting points.

In one embodiment, the biomedical implant further includes a pharmaceutical agent incorporated to the tubular scaffold. In a refinement, the pharmaceutical agent is a macrolide immunosuppressant. In a further refinement, the macrolide immunosuppressant is rapamycin or a derivative, a prodrug, a hydrate, an ester, a salt, a polymorph, a derivative or an analog thereof. In another further refinement, the macrolide immunosuppressant is selected from the group consisting of rapamycin, 40-O-(2-Hydroxyethyl)rapamycin, (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin. In one refinement, the pharmaceutical agent is rapamycin.

In one refinement, the pharmaceutical agent is impregnated in at least a portion of the tubular scaffold. In a further refinement, the pharmaceutical agent is impregnated in the polymer struts. In a further refinement, the pharmaceutical agent is evenly distributed throughout the polymer struts.

In one refinement, at least a portion of the tubular scaffold is covered with a coating comprising the pharmaceutical agent. In a further refinement, the coating further comprises a coating polymer. In a further refinement, at least 90% of the surface area of the pharmaceutical agent is encapsulated in the coating polymer. In a further refinement, the coating polymer comprises a bioabsorbable polymer. In a further refinement, the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyarginine, and mixtures or co-polymers thereof. In a further refinement, the biodegradable polymer is selected from the group consisting of PLGA, polyarginine, and mixtures thereof.

In one embodiment, the biomedical implant is a vascular stent. In another embodiment, the biomedical implant is a coronary artery stent. In another embodiment, the biomedical implant is a peripheral artery stent. In another embodiment, the biomedical implant is a non-vascular stent. In a refinement, the non-vascular stent is selected from esophageal stent, biliary stent, duodenal stent, colonic stent, and pancreatic stent.

According to another aspect of the present disclosure, a method of forming a gel-spun polyester fiber is provided. The method includes the steps of forming a gel composition comprising the polyester and a solvent; extruding the gel composition through one or more orifices into a stream of drying air; and allowing the solvent to evaporate in the drying air to form the polyester fiber. In a refinement, the method further includes the step of drawing the extruded polymer.

In one embodiment, the method further includes the step of cooling the polyester fiber in a liquid bath.

In one embodiment, the gel composition is extruded through a spinneret.

In one embodiment, the polyester is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); poly(d-lactide) (DPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), poly(lactic acid-co-caprolactone) (PLACL), and mixtures or co-polymers thereof. In a refinement, the polyester is PLGA. In another refinement, the polyester is PLA or LPLA.

According to another aspect of the present disclosure, a method of forming a liquid crystalline polyester fiber is provided. The method includes the steps of forming a liquid crystalline composition comprising the polyester; and extruding the liquid crystalline composition to form the polyester fiber.

In one embodiment, the polyester is in a melted state and wherein the method further comprises cooling the polyester fiber.

In one embodiment, the liquid crystalline composition further comprises a solvent and wherein the method further comprises allowing the solvent to evaporate.

In one embodiment, the polyester is selected from the group consisting of polylactides (PLA); poly(dl-lactide) (DLPLA); poly(l-lactide) (LPLA); poly(d-lactide) (DPLA); polyglycolide (PGA); poly(dioxanone) (PDO); poly(l-lactide-co-glycolide) (PGA-LPLA); poly(l-lactide-co-dl-lactide) (LPLA-DLPLA), poly(lactic acid-co-caprolactone) (PLACL), and mixtures or co-polymers thereof. In a refinement, the polyester is PLA. In another refinement, the polyester is LPLA. In another refinement, the polyester is PGA.

In some embodiments of the disclosed method of forming a gel-spun polyester fiber and/or forming a liquid crystalline polyester fiber, the polyester fiber has anisotropic elastic modulus. In a refinement, the polyester fiber comprises substantially aligned polymer chains.

According to another aspect of the present disclosure, a method of forming a biomedical implant is disclosed. The method includes the steps of forming one or more polymer fibers comprising longitudinally aligned polymer chains; and interconnecting the polymer fibers to form a tubular scaffold, the tubular scaffold comprising a plurality of interconnected polymer struts to define a plurality of deformable cells.

In one embodiment, the tubular scaffold maintains at least 50% of its nominal luminal cross sectional area under a pressure load of 50 mmHg. In another embodiment, the tubular scaffold maintains at least 80% of its nominal luminal cross sectional area under a pressure load of 50 mmHg.

In one embodiment, the tubular scaffold is form from a plurality of sinusoidal polymer fibers. In a refinement, the sinusoidal polymer fibers are interconnected at a plurality of connecting points.

In one embodiment, the tubular scaffold is formed from a single polymer fiber. In a refinement, the single polymer fiber comprises a plurality of sinusoidal sections interconnected at a plurality of connecting points.

In one embodiment, the one or more polymer fibers comprise gel-spun polyester. In a refinement, the polyester is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); poly(d-lactide) (DPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), poly(lactic acid-co-caprolactone) (PLACL), and mixtures or co-polymers thereof. In a further refinement, the polyester is PLGA. In another further refinement, the polyester is PLA or LPLA.

In one embodiment, the one or more polymer fibers comprise liquid crystalline polyester. In a refinement, the polyester is selected from the group consisting of polylactides (PLA); poly(dl-lactide) (DLPLA); poly(l-lactide) (LPLA); poly(d-lactide) (DPLA); polyglycolide (PGA); poly(dioxanone) (PDO); poly(l-lactide-co-glycolide) (PGA-LPLA); poly(l-lactide-co-dl-lactide) (LPLA-DLPLA), poly(lactic acid-co-caprolactone) (PLACL), and mixtures or co-polymers thereof. In a further refinement, the polyester is PLA. In another further refinement, the polyester is LPLA. In another further refinement, the polyester is PGA.

In one embodiment, the one or more polymer fibers have anisotropic elastic modulus.

In one embodiment, the method further includes the step of coating at least a portion of the tubular scaffold with a composition comprising a pharmaceutical agent. In a refinement, the composition further comprises a coating polymer. In further refinement, at least 90% of the surface area of the pharmaceutical agent is encapsulated in the coating polymer. In a further refinement, the coating polymer comprises a bioabsorbable polymer. In a further refinement, the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyarginine, and mixtures or co-polymers thereof. In a further refinement, the biodegradable polymer is selected from the group consisting of PLGA, polyarginine, and mixtures thereof.

In one embodiment, the one or more polymer fibers are gel-spun from a gel composition comprising the polymer and a pharmaceutical agent. In one embodiment, the one or more polymer fibers are extruded from a liquid crystalline composition comprising the polymer and a pharmaceutical agent.

In a refinement, the pharmaceutical agent is a macrolide immunosuppressant. In a further refinement, the macrolide immunosuppressant is rapamycin or a derivative, a prodrug, a hydrate, an ester, a salt, a polymorph, a derivative or an analog thereof. In another further refinement, the macrolide immunosuppressant is selected from the group consisting of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin. In a further refinement, the pharmaceutical agent is rapamycin.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE DISCLOSURE

The present disclosure is explained in greater detail below. This description is not intended to be a detailed catalog of all the different ways in which the present disclosure may be implemented, or all the features that may be added to the present disclosure. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the present disclosure. Hence, the following specification is intended to illustrate some particular embodiments of the present disclosure, and not to exhaustively specify all permutations, combinations and variations thereof.

Bioabsorbable Biomedical Implant

Fully bioabsorbable biomedical implants, such as stents made of polymers without metal structural reinforcements, provide several desirable features over metal-based biomedical implants. Yet, the development of fully bioabsorbable polymer stents remains challenging to this date. As bioabsorbable polymer materials used to make the polymer stents are generally weaker than metals (e.g. steel), polymer stents with structural strength and integrity similar to metal stents need to be made of polymer struts with average thickness much greater than that of the metal struts (e.g. greater or significantly greater than 120 µm).

It is contemplated in the present disclosure that the increased strut thickness, while improving the structural strength and integrity of the stents, may adversely affect one or more desirable characteristics of the polymer stent. For example, the thicker struts may result in a stent with larger overall stent profile and less flexibility, and hence more difficult to navigate within blood vessels before deployment. The thicker struts may also lead to lower deformability that limits range of deployment (e.g. less than 10% overexpansion above nominal diameter, or less than about 0.5 mm in a vascular stent). In addition, the thicker struts may take longer to be fully dissolved or degraded, such as between three to five years.

According to one aspect of the present disclosure, a biomedical implant is disclosed as including a tubular scaffold comprising a plurality of interconnected polymer struts. The interconnected polymer struts defines a plurality of deformable cells. The polymer struts have an average thickness of no more than 120 µm.

Average Strut Thickness

In one embodiment, the polymer struts have an average thickness of no more than 100 µm. In another embodiment, the polymer struts have an average thickness of no more than 90 µm. In another embodiment, the polymer struts have an average thickness of no more than 80 µm. In another embodiment, the polymer struts have an average thickness of no more than 70 µm. In another embodiment, the polymer struts have an average thickness of no more than 60 µm. In another embodiment, the polymer struts have an average thickness of no more than 50 µm.

In one embodiment, the polymer struts have an average thickness of from 50 µm to about 120 µm. In one embodiment, the polymer struts have an average thickness of from 60 µm to about 120 µm. In one embodiment, the polymer struts have an average thickness of from 70 µm to about 120 µm. In one embodiment, the polymer struts have an average thickness of from 80 µm to about 120 µm. In one embodiment, the polymer struts have an average thickness of from 90 µm to about 120 µm. In one embodiment, the polymer struts have an average thickness of from 100 µm to about 120 µm.

In one embodiment, the polymer struts have an average thickness of from 50 µm to about 100 µm. In one embodiment, the polymer struts have an average thickness of from 60 µm to about 100 µm. In one embodiment, the polymer struts have an average thickness of from 70 µm to about 100 µm. In one embodiment, the polymer struts have an average thickness of from 80 µm to about 100 µm. In one embodiment, the polymer struts have an average thickness of from 90 µm to about 100 µm.

In one embodiment, the polymer struts have an average thickness of from 50 µm to about 90 µm. In one embodiment, the polymer struts have an average thickness of from 60 µm to about 90 µm. In one embodiment, the polymer struts have an average thickness of from 70 µm to about 90 µm. In one embodiment, the polymer struts have an average thickness of from 80 µm to about 90 µm.

In one embodiment, the polymer struts have an average thickness of from 50 μm to about 80 μm. In one embodiment, the polymer struts have an average thickness of from 60 μm to about 80 μm. In one embodiment, the polymer struts have an average thickness of from 70 μm to about 80 μm.

Structural Strength and Integrity

The structural strength and integrity of the disclosed bioabsorbable biomedical implants can be characterized by one or combinations of the following methods.

Radial Strength Testing

This test is conducted to determine and graphically represent the change in stent internal diameter as a function of circumferential pressure and to determine the pressure at which deformation is no longer completely reversible for the disclosed stent. The stents are deployed to nominal pressure and removed from the delivery system. The stents are placed into a sleeve approximately 1 mm larger than the stent diameter. A vacuum is then applied and outer diameter measurements taken at various pressures. The bioabsorbable implants according to the present disclosure should maintain a minimum of at least 50 percent of the original stent diameter after a 50 mm Hg pressure is applied. Some bioabsorbable implants according to the present disclosure should maintain a minimum of at least 80 percent of the original stent diameter after a 50 mm Hg pressure is applied.

Stent Recoil Testing

This test was conducted to quantify the amount of elastic recoil. The stent delivery system is inflated to nominal pressure (9ATM) and the stent is removed allowing for recoil to occur. The inner diameter at each end of the stent is recorded. Recoil is calculated subtracting the recoiled stent inner diameter from the pre-recoil inner diameter.

Stent Expansion Testing

This test is conducted to determine if the plastic deformation experienced by the stent when expanded from the compressed profile to the final maximum deployed diameter (i.e. over-deployed diameter) can produce crack initiation for the disclosed stent. The sample stents are deployed to their largest possible diameters by inflating each delivery system to balloon failure. Each stent is examined at 45× magnification for potential cracks.

Maximum Pressure (Burst Test) Testing

This test is conducted to demonstrate that the delivery system (with mounted stent) will not experience balloon, shaft, proximal adaptation or proximal/distal seal loss of integrity at or below the pressure required to expand the stent to its labeled diameter. Stent delivery systems that had been subjected to all manufacturing and sterilization procedures were pressurized to 90 psi with pressure held for 15 seconds and released for 3 seconds. The cycle was then repeated, increasing inflation pressure by 15 psi each cycle until failure.

In one embodiment, the tubular scaffold maintains at least 50% of its nominal luminal cross sectional area under a pressure load of 50 mmHg. In another embodiment, the tubular scaffold maintains at least 60% of its nominal luminal cross sectional area under a pressure load of 50 mmHg. In another embodiment, the tubular scaffold maintains at least 70% of its nominal luminal cross sectional area under a pressure load of 50 mmHg. In another embodiment, the tubular scaffold maintains at least 80% of its nominal luminal cross sectional area under a pressure load of 50 mmHg. In another embodiment, the tubular scaffold maintains at least 90% of its nominal luminal cross sectional area under a pressure load of 50 mmHg. In another embodiment, the tubular scaffold maintains at least 95% of its nominal luminal cross sectional area under a pressure load of 50 mmHg.

In one embodiment, the tubular scaffold maintains at least 50% of its nominal luminal cross sectional area under a pressure load of 50 mmHg upon 2 months of exposure to saline in vitro. In another embodiment, the tubular scaffold maintains at least 50% of its nominal luminal cross sectional area under a pressure load of 50 mmHg upon 2 month in vivo.

In one embodiment, the tubular scaffold maintains at least 50% of its nominal luminal cross sectional area under a pressure load of 50 mmHg upon 3 months of exposure to saline in vitro. In another embodiment, the tubular scaffold maintains at least 50% of its nominal luminal cross sectional area under a pressure load of 50 mmHg upon 3 month in vivo.

In one embodiment, the tubular scaffold maintains at least 50% of its nominal luminal cross sectional area under a pressure load of 50 mmHg upon 4 months of exposure to saline in vitro. In another embodiment, the tubular scaffold maintains at least 50% of its nominal luminal cross sectional area under a pressure load of 50 mmHg upon 4 month in vivo.

In one embodiment, the tubular scaffold maintains at least 50% of its nominal luminal cross sectional area under a pressure load of 50 mmHg upon 6 months of exposure to saline in vitro. In another embodiment, the tubular scaffold maintains at least 50% of its nominal luminal cross sectional area under a pressure load of 50 mmHg upon 6 month in vivo.

Polymer Chain Orientation

Strut-Longitudinal Orientation

In one embodiment, each polymer strut includes polymer chains that are longitudinally aligned along a center axis of the polymer strut. In one embodiment, the polymer struts include crystalline domains, in which the polymer chains are longitudinally aligned along the center axes of the polymer struts. In another embodiment, more than 50% of polymer chains in the polymer struts or the crystalline domains are longitudinally aligned along the center axes of the polymer struts. In another embodiment, more than 55% of the polymer chains or the crystalline domains in the polymer struts are longitudinally aligned along the center axes of the polymer struts. In another embodiment, more than 60% of the polymer chains in the polymer struts or the crystalline domains are longitudinally aligned along the center axes of the polymer struts. In another embodiment, more than 65% of the polymer chains in the polymer struts or the crystalline domains are longitudinally aligned along the center axes of the polymer struts. In another embodiment, more than 70% of the polymer chains in the polymer struts or the crystalline domains are longitudinally aligned along the center axes of the polymer struts. In another embodiment, more than 75% of the polymer chains in the polymer struts or the crystalline domains are longitudinally aligned along the center axes of the polymer struts. In another embodiment, more than 80% of the polymer chains in the polymer struts or the crystalline domains are longitudinally aligned along the center axes of the polymer struts. In another embodiment, more than 85% of the polymer chains in the polymer struts or the crystalline domains are longitudinally aligned along the center axes of the polymer struts. In another embodiment, more than 90% of the polymer chains in the polymer struts or the crystalline domains are longitudinally aligned along the center axes of the polymer struts. In another embodiment, more than 95% of the polymer chains in the polymer struts or the crystalline domains are longitudinally aligned along the center axes of the polymer struts.

As a result of the strut-longitudinal polymer chain orientation, the polymer struts have anisotropic elastic modulus. For example, the polymer struts have an average longitudinal elastic modulus along the center axes of the polymer struts and an average lateral elastic modulus orthogonal to the center axes of the polymer struts, the average longitudinal elastic modulus being greater than the average lateral elastic modulus.

In one embodiment, the average longitudinal elastic modulus is at least 2 times the average lateral elastic modulus. In another embodiment, the average longitudinal elastic modulus is at least 3 times the average lateral elastic modulus. In another embodiment, the average longitudinal elastic modulus is at least 4 times the average lateral elastic modulus. In another embodiment, the average longitudinal elastic modulus is at least 5 times the average lateral elastic modulus. In another embodiment, the average longitudinal elastic modulus is at least 6 times the average lateral elastic modulus. In another embodiment, the average longitudinal elastic modulus is at least 7 times the average lateral elastic modulus. In another embodiment, the average longitudinal elastic modulus is at least 8 times the average lateral elastic modulus. In another embodiment, the average longitudinal elastic modulus is at least 9 times the average lateral elastic modulus. In another embodiment, the average longitudinal elastic modulus is at least 10 times the average lateral elastic modulus.

Scaffold-Axial Orientation

In one embodiment, the tubular scaffold includes polymer chains that are axially aligned along a center axis of the tubular scaffold. In one embodiment, the polymer struts include crystalline domains, in which the polymer chains are axially aligned along a center axis of the tubular scaffold. In another embodiment, more than 50% of polymer chains in the polymer struts or the crystalline domains are axially aligned along a center axis of the tubular scaffold. In another embodiment, more than 55% of the polymer chains or the crystalline domains in the polymer struts are axially aligned along a center axis of the tubular scaffold. In another embodiment, more than 60% of the polymer chains in the polymer struts or the crystalline domains are axially aligned along a center axis of the tubular scaffold. In another embodiment, more than 65% of the polymer chains in the polymer struts or the crystalline domains are axially aligned along a center axis of the tubular scaffold. In another embodiment, more than 70% of the polymer chains in the polymer struts or the crystalline domains are axially aligned along a center axis of the tubular scaffold. In another embodiment, more than 75% of the polymer chains in the polymer struts or the crystalline domains are axially aligned along a center axis of the tubular scaffold. In another embodiment, more than 80% of the polymer chains in the polymer struts or the crystalline domains are axially aligned along a center axis of the tubular scaffold. In another embodiment, more than 85% of the polymer chains in the polymer struts or the crystalline domains are axially aligned along a center axis of the tubular scaffold. In another embodiment, more than 90% of the polymer chains in the polymer struts or the crystalline domains are axially aligned along a center axis of the tubular scaffold. In another embodiment, more than 95% of the polymer chains in the polymer struts or the crystalline domains are axially aligned along a center axis of the tubular scaffold.

As a result of the scaffold-axial polymer chain orientation, the tubular scaffold has anisotropic elastic modulus. For example, the tubular scaffold has an average axial elastic modulus along a center axis of the tubular scaffold and an average circumferential elastic modulus orthogonally surrounding a center axis of the tubular scaffold, the average axial elastic modulus being greater than the average circumferential elastic modulus.

In one embodiment, the average axial elastic modulus is at least 2 times the average circumferential elastic modulus. In another embodiment, the average axial elastic modulus is at least 3 times the average circumferential elastic modulus. In another embodiment, the average axial elastic modulus is at least 4 times the average circumferential elastic modulus. In another embodiment, the average axial elastic modulus is at least 5 times the average circumferential elastic modulus. In another embodiment, the average axial elastic modulus is at least 6 times the average circumferential elastic modulus. In another embodiment, the average axial elastic modulus is at least 7 times the average circumferential elastic modulus. In another embodiment, the average axial elastic modulus is at least 8 times the average circumferential elastic modulus. In another embodiment, the average axial elastic modulus is at least 9 times the average circumferential elastic modulus. In another embodiment, the average axial elastic modulus is at least 10 times the average circumferential elastic modulus.

Scaffold-Circumferential Orientation

In one embodiment, the tubular scaffold includes polymer chains that are circumferential aligned, i.e. orthogonally surrounding a center axis of the tubular scaffold. In one embodiment, the polymer struts include crystalline domains, in which the polymer chains are circumferential aligned. In another embodiment, more than 50% of polymer chains in the polymer struts or the crystalline domains are circumferential aligned. In another embodiment, more than 55% of the polymer chains or the crystalline domains in the polymer struts are circumferential aligned. In another embodiment, more than 60% of the polymer chains in the polymer struts or the crystalline domains are circumferential aligned. In another embodiment, more than 65% of the polymer chains in the polymer struts or the crystalline domains are circumferential aligned. In another embodiment, more than 70% of the polymer chains in the polymer struts or the crystalline domains are circumferential aligned. In another embodiment, more than 75% of the polymer chains in the polymer struts or the crystalline domains are circumferential aligned. In another embodiment, more than 80% of the polymer chains in the polymer struts or the crystalline domains are circumferential aligned. In another embodiment, more than 85% of the polymer chains in the polymer struts or the crystalline domains are circumferential aligned. In another embodiment, more than 90% of the polymer chains in the polymer struts or the crystalline domains are circumferential aligned. In another embodiment, more than 95% of the polymer chains in the polymer struts or the crystalline domains are circumferential aligned.

As a result of the scaffold-circumferential polymer chain orientation, the tubular scaffold has anisotropic elastic modulus. For example, the tubular scaffold has an average axial elastic modulus along a center axis of the tubular scaffold and an average radial elastic modulus orthogonal to a center axis of the tubular scaffold, the average circumferential elastic modulus being greater than the average axial elastic modulus.

In one embodiment, the average circumferential elastic modulus is at least 2 times the average axial elastic modulus. In another embodiment, the average circumferential elastic modulus is at least 3 times the average axial elastic modulus. In another embodiment, the average circumferential elastic modulus is at least 4 times the average axial elastic modulus. In another embodiment, the average circumferential elastic modulus is at least 5 times the average axial elastic modulus. In another embodiment, the average circumferential elastic modulus is at least 6 times the average axial elastic modulus. In another embodiment, the average circumferential elastic modulus is at least 7 times the average axial elastic modulus. In another embodiment, the average circumferential elastic modulus is at least 8 times the average axial elastic modulus. In another embodiment, the average circumferential elastic modulus is at least 9 times the average axial elastic modulus. In another embodiment, the average circumferential elastic modulus is at least 10 times the average axial elastic modulus.

Deformation Angle

Further, as a result of the polymer chain orientation, the polymer struts have an average deformation angle, i.e the average angle between the polymer struts when deployed minus the average angle between the polymer struts when undeployed. In one embodiment, the polymer struts have an average deformation angle of at least 90 degrees. In another embodiment, the polymer struts have an average deformation angle of at least 85 degrees. In another embodiment, the polymer struts have an average deformation angle of at least 80 degrees. In another embodiment, the polymer struts have an average deformation angle of at least 75 degrees. In another embodiment, the polymer struts have an average deformation angle of at least 70 degrees. In another embodiment, the polymer struts have an average deformation angle of at least 65 degrees. In another embodiment, the polymer struts have an average deformation angle of at least 60 degrees. In another embodiment, the polymer struts have an average deformation angle of at least 55 degrees. In another embodiment, the polymer struts have an average deformation angle of at least 50 degrees. In another embodiment, the polymer struts have an average deformation angle of at least 45 degrees. In another embodiment, the polymer struts have an average deformation angle of at least 40 degrees. In another embodiment, the polymer struts have an average deformation angle of at least 30 degrees. Without wishing to be bound by any particular theory, it is contemplated that the configuration of the polymer struts according to the specified deformation angle improves the deformability of the polymer stent made of chain-oriented polymers.

Bioabsorbable Polymer Materials

In one embodiment, the polymer struts comprises a gel-spun polymer material. In a refinement, the polymer struts are not structurally reinforced with a metal material. In a further refinement, the gel-spun polymer material is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); poly(d-lactide) (DPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), poly(lactic acid-co-caprolactone) (PLACL), and mixtures or co-polymers thereof.

In one refinement, the gel-spun polymer material is PLGA. In a further refinement, the PLGA has a ratio of lactic acid monomer to glycolic acid monomer ranging from 82:18 to 88:12. In a further refinement, the PLGA has a ratio of lactic acid monomer to glycolic acid monomer ranging from 72:28 to 78:22. In another further refinement, the PLGA has a ratio of lactic acid monomer to glycolic acid monomer ranging from 62:38 to 68:32. In another further refinement, the PLGA has a ratio of lactic acid monomer to glycolic acid monomer ranging from 47:53 to 53:47. In another further refinement, the PLGA has a ratio of lactic acid monomer to glycolic acid monomer of 50:50.

In another further refinement, the PLGA has a weight average molecular weight of about 8,000 Dalton to about 12,000 Dalton. In another further refinement, the PLGA has a weight average molecular weight of about 12,000 Dalton to about 16,000 Dalton. In another further refinement, the PLGA has a weight average molecular weight of up to about 90,000 Dalton. In another refinement, the gel-spun polymer material is PLA or LPLA. In another refinement, the gel-spun polymer material is PGA. In some embodiment, the gel spun polymer material (e.g. PLGA, LPLA, PLA, PGA) has a weight average molecular weight of at least 90,000 Dalton, and optionally at least 100,000 Dalton In one embodiment, the polymer struts comprises a liquid crystalline polymer material. In a refinement, the liquid crystalline polymer material is drawn from a liquid crystalline melt or solution. In another refinement, the polymer struts are not structurally reinforced with a metal material. In a further refinement, the liquid crystalline polymer material is selected from the group consisting of polylactides (PLA); poly(dl-lactide) (DLPLA); poly(l-lactide) (LPLA); poly(d-lactide) (DPLA); polyglycolide (PGA); poly(dioxanone) (PDO); poly(l-lactide-co-glycolide) (PGA-LPLA); poly(l-lactide-co-dl-lactide) (LPLA-DLPLA), poly(lactic acid-co-caprolactone) (PLACL), and mixtures or co-polymers thereof.

In another refinement, the liquid crystalline polymer material has a crystallinity of at least 30%. In another refinement, the liquid crystalline polymer material has a crystallinity of at least 35%. In another refinement, the liquid crystalline polymer material has a crystallinity of at least 40%. In another refinement, the liquid crystalline polymer material has a crystallinity of at least 45%. In another refinement, the liquid crystalline polymer material has a crystallinity of at least 50%. In another refinement, the liquid crystalline polymer material has a crystallinity of at least 55%. In another refinement, the liquid crystalline polymer material has a crystallinity of at least 60%. In another refinement, the liquid crystalline polymer material has a crystallinity of at least 65%. In another refinement, the liquid crystalline polymer material has a crystallinity of at least 70%.

In another refinement, the liquid crystalline polymer material is PLA or LPLA. In another refinement, the liquid crystalline polymer material is PGA. In some embodiment, the liquid crystalline polymer material (e.g. LPLA, PLA, PGA) has a weight average molecular weight of at least 90,000 Dalton, and optionally at least 100,000 Dalton In one embodiment, the polymer struts include a polymer material selected from the group consisting of polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)

s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof.

Stent Deployment

In one embodiment, the tubular scaffold is expandable from an undeployed diameter to a nominal diameter without affecting the structural integrity of the tubular scaffold. In a refinement, the tubular scaffold is further expandable from the nominal diameter to an over-deployed diameter without affecting the structural integrity of the tubular scaffold.

In a further refinement, the over-deployed diameter is about 1.0 mm greater than the nominal diameter. In another further refinement, the over-deployed diameter is about 0.9 mm greater than the nominal diameter. In another further refinement, the over-deployed diameter is about 0.8 mm greater than the nominal diameter. In another further refinement, the over-deployed diameter is about 0.7 mm greater than the nominal diameter. In another further refinement, the over-deployed diameter is about 0.6 mm greater than the nominal diameter. In another further refinement, the over-deployed diameter is about 0.5 mm greater than the nominal diameter. In another further refinement, the over-deployed diameter is about 0.4 mm greater than the nominal diameter. In another further refinement, the over-deployed diameter is about 0.3 mm greater than the nominal diameter. In another further refinement, the over-deployed diameter is about 0.2 mm greater than the nominal diameter.

In one refinement, the tubular scaffold is expandable by an inflatable balloon positioned within the tubular scaffold. In a further refinement, the tubular scaffold has a deployed diameter of 2.25 mm at nominal balloon pressure. In another further refinement, the tubular scaffold has a deployed diameter of 2.5 mm at nominal balloon pressure. In another further refinement, the tubular scaffold has a deployed diameter of 3.0 mm at nominal balloon pressure. In another further refinement, the tubular scaffold has a deployed diameter of 3.5 mm at nominal balloon pressure. In another further refinement, the tubular scaffold has a deployed diameter of 4.0 mm at nominal balloon pressure. In another further refinement, the tubular scaffold has a deployed diameter of 4.5 mm at nominal balloon pressure. The nominal balloon pressure may be dependent on the material and design of the balloon. As a non-limiting example, the nominal balloon pressure is 6 atmospheres. As another example, the nominal balloon pressure is 9 atmosphere.

In one refinement, the polymer struts comprise a shape-memory polymer and wherein tubular scaffold is self-expandable. In a further refinement, the tubular scaffold is self-expandable upon change in temperature. In another further refinement, the tubular scaffold is self-expandable upon change in crystallinity of the shape-memory polymer.

In one embodiment, the tubular scaffold is formed from a plurality of sinusoidal polymer fibers. In a refinement, the sinusoidal polymer fibers are interconnected at a plurality of connecting points.

In one embodiment, the tubular scaffold is formed from a single polymer fiber. In a refinement, the single polymer fiber comprises a plurality of sinusoidal sections interconnected at a plurality of connecting points.

Many methods for forming wire- or filament-based stents can be used to make the bioabsorbable stents disclosed herein. For example, the methods for forming Wallstent (Boston Scientific), S7 (Medtronic), AngioStent (AngioDynamics), Strecker (Boston Scientific), Expander (Medicorp), Horizon Prostatic (Endocare), Endocoil (InStent), etc, can be used to in light of the present disclosure.

Drug Coating

In one embodiment, the biomedical implant further includes a pharmaceutical agent incorporated to the tubular scaffold. In a refinement, the pharmaceutical agent is a macrolide immunosuppressant. In a further refinement, the macrolide immunosuppressant is rapamycin or a derivative, a prodrug, a hydrate, an ester, a salt, a polymorph, a derivative or an analog thereof. In another further refinement, the macrolide immunosuppressant is selected from the group consisting of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin. In one refinement, the pharmaceutical agent is rapamycin.

In one refinement, the pharmaceutical agent is impregnated in at least a portion of the tubular scaffold. In a further refinement, the pharmaceutical agent is impregnated in the polymer struts. In a further refinement, the pharmaceutical agent is evenly distributed throughout the polymer struts.

In one refinement, at least a portion of the tubular scaffold is covered with a coating comprising the pharmaceutical agent. In a further refinement, the coating further comprises a coating polymer. In a further refinement, at least 90% of the surface area of the pharmaceutical agent is encapsulated in the coating polymer. In a further refinement, at least 85% of the surface area of the pharmaceutical agent is encapsulated in the coating polymer. In a further refinement, at least 80% of the surface area of the pharmaceutical agent is encapsulated in the coating polymer. In a further refinement, at least 75% of the surface area of the pharmaceutical agent is encapsulated in the coating polymer. In a further refinement, at least 70% of the surface area of the pharmaceutical agent is encapsulated in the coating polymer. In a further refinement, at least 65% of the surface area of the pharmaceutical agent is encapsulated in the coating polymer. In a further refinement, at least 60% of the surface area of the pharmaceutical agent is encapsulated in the coating polymer. In a further refinement, at least 55% of the surface area of the pharmaceutical agent is encapsulated in the coating polymer. In a further refinement, at least 50% of the surface area of the pharmaceutical agent is encapsulated in the coating polymer.

In a further embodiment, the pharmaceutical agent is impregnated in at least a portion of the tubular scaffold (e.g. evenly distributed throughout the tubular scaffold) and at least a portion of the tubular scaffold is covered with a coating comprising the pharmaceutical agent, such as in the manner discussed in the paragraph above.

In a further refinement, the coating polymer comprises a bioabsorbable polymer. In a further refinement, the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyarginine, and mixtures or co-polymers thereof. In a further refinement, the biodegradable polymer is selected from the group consisting of PLGA, polyarginine, and mixtures thereof.

In one embodiment, the biomedical implant is a vascular stent. In another embodiment, the biomedical implant is a coronary artery stent. In another embodiment, the biomedical implant is a peripheral artery stent. In another embodiment, the biomedical implant is a non-vascular stent. In a refinement, the non-vascular stent is selected from esophageal stent, biliary stent, duodenal stent, colonic stent, and pancreatic stent.

Gel-Spun Polymer

According to another aspect of the present disclosure, a method of forming a gel-spun polyester fiber is provided. The method includes the steps of forming a gel composition comprising the polyester and a solvent; extruding the gel composition through one or more orifices into a stream of drying air; and allowing the solvent to evaporate in the drying air to form the polyester fiber. In a refinement, the method further includes the step of drawing the extruded polymer.

In one embodiment, the method further includes the step of cooling the polyester fiber in a liquid bath.

In one embodiment, the gel composition are extruded through a spinneret.

In one embodiment, the polyester is selected from the group consisting of polylactides (PLA); poly(lactide-co-glycolide) (PLGA); polyanhydrides; polyorthoesters; poly (N-(2-hydroxypropyl) methacrylamide); poly(dl-lactide) (DLPLA); poly(l-lactide) (LPLA); poly(d-lactide) (DPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), poly(lactic acid-co-caprolactone) (PLACL), and mixtures or co-polymers thereof. In a refinement, the polyester is PLGA. In another refinement, the polyester is PLA or LPLA.

Liquid Crystalline Polyester

According to another aspect of the present disclosure, a method of forming a liquid crystalline polyester fiber is provided. The method includes the steps of forming a liquid crystalline composition comprising the polyester; and extruding the liquid crystalline composition to form the polyester fiber.

In one embodiment, the polyester is in a melted state and wherein the method further comprises cooling the polyester fiber.

In one embodiment, the liquid crystalline composition further comprises a solvent and wherein the method further comprises allowing the solvent to evaporate.

In one embodiment, the polyester is selected from the group consisting of polylactides (PLA); poly(dl-lactide) (DLPLA); poly(l-lactide) (LPLA); poly(d-lactide) (DPLA); polyglycolide (PGA); poly(dioxanone) (PDO); poly(l-lactide-co-glycolide) (PGA-LPLA); poly(l-lactide-co-dl-lactide) (LPLA-DLPLA), poly(lactic acid-co-caprolactone) (PLACL), and mixtures or co-polymers thereof. In a refinement, the polyester is PLA. In another refinement, the polyester is LPLA. In another refinement, the polyester is PGA.

In some embodiments of the disclosed method of forming a gel-spun polyester fiber and/or forming a liquid crystalline polyester fiber, the polyester fiber has anisotropic elastic modulus. In a refinement, the polyester fiber comprises substantially aligned polymer chains.

Manufacturing of Bioabsorbable Stent

According to another aspect of the present disclosure, a method of forming a biomedical implant is disclosed. The method includes the steps of forming one or more polymer fibers comprising longitudinally aligned polymer chains; and interconnecting the polymer fibers to form a tubular scaffold, the tubular scaffold comprising a plurality of interconnected polymer struts to define a plurality of deformable cells.

Manufacturing of Tubular Scaffold

Tubular Scaffold with Strut-Longitudinally Aligned Polymer Orientation

In this non-limiting example, the tubular scaffold of the present disclosure is made by forming a continuous wave form that includes a plurality of struts and a plurality of crowns. Each crown is a curved portion or turn within the wave form that connects adjacent struts to define the continuous wave form. In this example, the struts are substantially straight portions of the wave form. In other examples, the struts are slightly bent or have other shapes, such as a sinusoidal wave, for example. The wave form may be formed by a single polymer fiber or filament or a plurality of interconnected polymer fibers or filaments.

After the wave form is formed, the wave form is wrapped around a mandrel, a center axis of which defines the longitudinal axis of the tubular scaffold. The wave form may be wrapped at an angle that is not perpendicular to the longitudinal axis to form a plurality of helical turns that together generally form a helical coil in the shape of a helix.

The tubular scaffold also includes a plurality of connections that are configured to connect selected crowns of adjacent turns. In one embodiment, the tubular scaffold includes three connections per complete helix turn. In one embodiment, the tubular scaffold includes four connections per complete helix turn. In one embodiment, the tubular scaffold includes five connections per complete helix turn. Other connection numbers and configurations can also be used in light of the present disclosure. In a non-limiting example, the connections are created by fusing the selected crowns together. As used herein, "fusing" is defined as heating the target portions of materials to be fused together, with or without adding any additional material, to a level where the material in the target portions flow together, intermix with one another, and form a fusion when the materials cool down to, for example, room temperature.

Many methods for forming wire- or filament-based stents can be used to make the bioabsorbable stents disclosed herein. For example, the methods for forming Wallstent (Boston Scientific), S7 (Medtronic), AngioStent (AngioDynamics), Strecker (Boston Scientific), Expander (Medicorp), Horizon Prostatic (Endocare), Endocoil (InStent), etc, can be used to in light of the present disclosure Tubular Scaffold with Scaffold-Axially Aligned Polymer Orientation In this non-limiting example, the tubular scaffold of the present disclosure is made by forming polymer tube in which at least some polymer chains are aligned to a center axis of the polymer tube. In one embodiment, the polymer tube is formed by (1) forming a gel composition comprising the polymer and a solvent; (2) extruding the gel composition to form a tubular structure; and (3) allowing the solvent to evaporate in drying air to form the polyester fiber. In a refinement, the extruded polymer tube undergoes another drawing process. In another embodiment, the polymer tube is formed by (1) forming a liquid crystalline composition (e.g. a melt) containing the polymer; and (2) extruding the liquid crystalline composition to form a tubular structure. In a refinement, the extruded polymer tube undergoes another longitudinal drawing process.

After the polymer tube is formed, the tubular scaffold can be made by laser-cutting a stent design from the polymer tube. In one embodiment, the stent design is cut from the polymer tube using a polymer-compatible laser, such as carbon dioxide laser beam or other suitable laser cutting technologies in light of the present disclosure. In another embodiment, the stent design is cut from the polymer tube by water jet cutting or abrasive water jet cutting. Alternatively, the tubular scaffold can be made through photochemical etching or chemical etching. Many slotted tube stent designs can be used to make the bioabsorbable stents disclosed herein. For example, suitable stent deigns may include, but are not limited to, bStent2 by Medtronic; BiodivYsio by Biocompatibles Ltd.; Velocity, Palmaz-Schatz 153/154, Palmaz-Schatz Crown by Cordis; Express by Boston Scientific; JOSTENT Flex by JOMED; Multi-Link PENTA, Multi-Link Rx, and Multi-Link Vision by Guidant; and NIR and NIR Flex by Medinol. Other stent designs may also be used in light of the present disclosure.

Tubular Scaffold with Scaffold-Circumferentially Aligned Polymer Orientation

In this non-limiting example, the tubular scaffold of the present disclosure is made by first forming a polymer preform containing the bioabsorbable polymer material. In one embodiment, the polymer preform is molded or extruded from a gel composition containing the bioabsorbable polymer material. In another embodiment, the polymer preform is molded or extruded from a liquid crystalline composition containing the bioabsorbabel polymer material. The polymer preform is then radially expanded and/or stretched to desired inner diameter and wall thickness to form the polymer tube in which at least some polymer chains are circumferentially aligned (orthogonal to a center axis of the polymer tube). Without wishing to be bound by any particular theory, it is contemplated in the present disclosure that the radial expansion and stretching of the preform at least partially contribute to the circumferential alignment of the polymer chains in the polymer tube.

After the polymer tube is formed, the tubular scaffold can be made by laser-cutting a stent design from the polymer tube. In one embodiment, the stent design is cut from the polymer tube using a polymer-compatible laser, such as carbon dioxide laser beam or other suitable laser cutting technologies in light of the present disclosure. In another embodiment, the stent design is cut from the polymer tube by water jet cutting or abrasive water jet cutting. Alternatively, the tubular scaffold can be made through photochemical etching or chemical etching. Many slotted tube stent designs can be used to make the bioabsorbable stents disclosed herein. For example, suitable stent deigns may include, but are not limited to, bStent2 by Medtronic; BiodivYsio by Biocompatibles Ltd.; Velocity, Palmaz-Schatz 153/154, Palmaz-Schatz Crown by Cordis; Express by Boston Scientific; JOSTENT Flex by JOMED; Multi-Link PENTA, Multi-Link Rx, and Multi-Link Vision by Guidant; and NIR and NIR Flex by Medinol. Other stent designs may also be used in light of the present disclosure.

Coating of Tubular Scaffold.

Provided herein are methods for coating the tubular scaffold (also referred to as substrate in this section) with a pharmaceutical or biological agent in powder form. Conventional processes for spray coating stents may also be used. For example, the drug and coating polymer may be dissolved in a suitable solvent or mutual solvent before spray coating can occur. Provided herein are methods for depositing a coating polymer and a pharmaceutical or biological agent in powder form onto the substrate. The coating process provides a cost-effective, efficient method for depositing a combination of an inert polymer or polymers and a pharmaceutical or biological agent or agents, onto parts or all surfaces of a substrate, to form a coating that is of a pre-determined, desired thickness, conformal, substantially defect-free, and uniform and the composition of the coating can be regulated. In particular, the coating process addresses the problem of existing coating processes, which do not allow for structural and morphological preservation of the agents deposited during the coating process.

One aspect of the invention entails the deposition of the pharmaceutical or biological agents as dry powder. Dry powder spraying is well known in the art, and dry powder spraying coupled with electrostatic capture has been described, for example in U.S. Pat. Nos. 5,470,603; 6,319,541; or 6,372,246. The deposition of the polymer can be performed in any number of standard procedures, as the morphology of the polymer, so long as it provides coatings possessing the desired properties (e.g. thickness, conformity, defect-free, uniformity etc), is of less importance. The function of the polymer is primarily one of inert carrier matrix for the active components of the coating.

One aspect of the coating process is the combination of two or more of the dry powder, RESS and SEDS spraying techniques.

Another aspect of the coating process involves the dry powder spraying of a pharmaceutical agent, in a preferred particle size and morphology, into the same capture vessel as a polymer that is also dry powder sprayed, whereby the spraying of the agent and the polymer is sequential or simultaneous.

Another specific aspect of the coating process involves the dry powder spraying of an active biological agent, in a preferred particle size and possessing a particular activity, into the same capture vessel as a polymer that is also dry powder sprayed, whereby the spraying of the agent and the polymer is sequential or simultaneous.

Yet another aspect of the coating process involves the dry powder spraying of a pharmaceutical agent, in a preferred particle size and morphology, into the same capture vessel as a polymer that is sequentially or simultaneously sprayed by the RESS spray process.

Yet another aspect of the coating process involves the dry powder spraying of an active biological agent, in a preferred particle size and possessing a particular activity, into the same capture vessel as a polymer that is sequentially or simultaneously sprayed by the RESS spray process.

Yet another aspect of the coating process involves the dry powder spraying of a pharmaceutical agent, in a preferred particle size and morphology, into the same capture vessel as a polymer that is sequentially or simultaneously sprayed by the SEDS spray process.

Yet another aspect of the coating process involves the dry powder spraying of an active biological agent, in a preferred particle size and possessing a particular activity, into the same capture vessel as a polymer that is sequentially or simultaneously sprayed by the SEDS spray process.

In some embodiments, the RESS or the SEDS process used in forming the coating is performed with electrically charging the substrate. In some embodiments, the e-RESS or the e-SEDS process used in forming the coating is performed by creating an electrical potential between the substrate and the coating apparatus used in process. In some embodiment, the RESS or the SEDS process used in forming the coating is performed without electrically charging the substrate.

In further aspects of the coating process the substrates that have been coated with pharmaceutical or biological agents and polymers, as described in the above embodiments are then subjected to a sintering process. The sintering process takes place under benign conditions, which do not affect the structural and morphological integrity of the pharmaceutical and biological agents, and refers to a process by which the co-deposited pharmaceutical agent or biological agent-polymer matrix, becomes continuous and adherent to the substrate. This is achieved by treating the coated substrate with a compressed gas, compressed liquid or supercritical fluid at conditions such that it is a poor solvent of the polymers, a weak solvent of the polymers or a non-solvent for the polymers, the pharmaceutical agents and the biological agents, but an agent suitable for the treatment of polymer particles to form continuous polymer coatings. The sintering process takes place under conditions (e.g. mild temperatures), and using benign fluids (e.g. supercritical carbon dioxide) which will not affect the structural and morphological integrity of the pharmaceutical and biological agents. Other sintering processes, which do not affect the structural and morphological integrity of the pharmaceutical and biological agents may also be contemplated by the present invention.

In further aspects of the coating process, it is desirable to create coatings such that release of an active substance occurs with a predetermined elution profile when placed in the desired elution media. Coating properties can be modified in a variety of different ways in order to provide desirable elution profiles.

The chemical composition of the coating polymers can be varied, to provide greater or lesser amounts of coating polymers that will allow or restrict the elution of active substance. For example, if the intended elution media contain water, a higher content of coating polymers that swell in water, will allow for a faster elution of active substance. Conversely, a higher content of coating polymers that do not swell in aqueous media will result in a slower elution rate.

The coating properties can also be controlled by alternating coating polymer layers. Layers of coating polymers of different properties are deposited on the substrate in a sequential manner. By modifying the nature of the polymer deposited in each layer (e.g., depositing layers of different polymers) the elution profile of the coating is altered. The number of layers and the sequence in their deposition provide additional avenues for the design of coatings having controlled elution profiles.

The coating properties can also be modified by control of the macro and/or micro-structure of the polymer coating (diffusion pathways). This may be achieved by varying the coating process(es) or by using different sintering conditions.

The coating process provides several approaches for controlling the elution of a drug or several drugs. For example, in one embodiment, controlled elution is achieved by the segregation of different coating polymers (e.g. PEVA/PBMA). In another embodiment, control of elution is achieved by controlling the conditions during the sintering process such that controlled incomplete sintering of the polymer matrix is obtained, whereby the coating would retain some of the particle-like structure of the polymer particles as deposited. Incomplete sintering would provide pores/voids in the coating and allow additional pathways for elution of the drug, including drug elution around the polymer(s) instead of, or in addition to, elution through the polymer(s). The size of the pores or voids obtained through incomplete sintering of the polymer matrix may be obtained through several methods. For example, the rate of depressurization of a vessel in which the sintering process is carried out provides one avenue for controlling pore size. The size of the cavities or pores in the coating can be controlled by employing a porogen as an excipient and subsequent removal of at least a portion of the porogen, for example by treatment with a solvent of the porogen. Preferably, the porogen solvent comprises a densified gas (e.g.; carbon). In some embodiments the porogen is an SOA or other such hydrophobically derivatized carbohydrate. Removal of at least a portion of the porogen is preferably carried out during the sintering process.

In some aspects of the invention, the active substance elution profile is controllable by altering the coating polymer particle size. The method by which the polymer particles are deposited onto the substrate is thus varied to provide the desired elution rate. For example, for polymers released simultaneously through the same nozzle, RESS release from a supercritical solution would typically result in small polymer particles; RESS-like release from a mixture in a compressed gas usually generates larger polymer particles. Using the SEDS process can result in variable polymer particle size, depending on the particular SEDS conditions employed.

In further aspects of the coating process, the active substance elution profile is controllable by altering the coating polymer particle shape. One way to achieve variation in polymer particle shape is to alter the initial concentration of the polymers. At lower initial concentrations, polymers are deposited as small particles. At increased concentrations, larger particles are formed. At higher concentrations, the formed particles become elongated, until at high concentrations the elongated features become fiber-like and eventually become continuous fibers.

In yet other aspects of the coating process, the active substance elution profile is controllable by creating discrete domains of chemically different polymers. As described above, chemically different polymers will allow or restrict the elution of active substance in different elution media. By changing the position of such polymers in discrete macroscopic domains within the coating, the elution profiles will be adjustable. For example during a process whereby two different polymers are released sequentially through the same nozzle, particles of either polymer could be deposited to position them, for example, closer to the outside, the inside or the middle of the coating on the substrate. In another embodiment, the two polymers may be released simultaneously through two different nozzles at differing and/or alternating deposition rates, resulting in a similar effect. In a further embodiment, the deposition of eluting and non-eluting polymers is alternated to result in a fluctuating type of release. In yet other embodiments, the polymers are deposited to provide for a pulsatile release of active substance. Separation of the polymer(s) providing different domains for drug diffusion is achieved, for example, by subsequent spray of the polymers through same nozzle or by using multiple nozzles. Also, as described above, controlling the elution of the active substance may be achieved by layering of different polymers across the depth of the coating. A combination of domain separation and cross-depth layering is also contemplated for the design of coatings having controlled elution properties.

The deposition of active substance during any of these processes may be constant to provide even distribution throughout the coating, or the spraying of the active substance may be varied to result in differing amounts of active substance in the differing polymeric domains within the coating.

In further aspects of the coating process, the active substance elution profile is controllable by varying the coating sintering conditions. For example, incomplete sintering will create open spaces, or pores in the interstitial spaces between the polymer particles, which will enable faster eluting of active substance from the coating. Another way to utilize the sintering conditions for elution control would be to deliberately create irregular coatings by foaming during the sintering process. Rapid pressure release of a $CO_2$— or isobutylene-impregnated polymer film induces formation of foamed polymers which would create a coating with increased porosity and be very 'open' to diffusion/ elution. Thus the elution profile would be controllable by manipulating the foaming conditions, which in turn controls the pore density and size.

Another advantage of the coating process is the ability to create a stent with a controlled (dialed-in) drug-elution profile. Via the ability to have different materials in each layer of the laminate structure and the ability to control the location of drug(s) independently in these layers, the method enables a stent that could release drugs at very specific elution profiles, programmed sequential and/or parallel elution profiles. Also, the present invention allows controlled elution of one drug without affecting the elution of a second drug (or different doses of the same drug).

The embodiments incorporating a stent form or framework provide the ability to radiographically monitor the stent in deployment. In an alternative embodiment, the inner-diameter of the stent can be masked (e.g. by a non-conductive mandrel). Such masking would prevent additional layers from being on the interior diameter (abluminal) surface of the stent. The resulting configuration may be desirable to provide preferential elution of the drug toward the vessel wall (luminal surface of the stent) where the therapeutic effect of anti-restenosis is desired, without providing the same antiproliferative drug(s) on the abluminal surface, where they may retard healing, which in turn is suspected to be a cause of late-stage safety problems with current DESs.

The coating process allows for employing a platform combining layer formation methods based on compressed fluid technologies; electrostatic capture and sintering methods. The platform results in drug eluting stents having enhanced therapeutic and mechanical properties. The coating process is particularly advantageous in that it employs optimized laminate polymer technology. In particular, the coating process allows the formation of discrete layers of specific drug platforms.

The coating process provided herein the drugs and polymers are coated on the stent framework in discrete steps, which can be carried out simultaneously or alternately. This allows discrete deposition of the active agent (e.g.; a drug) within a polymer matrix thereby allowing the placement of more than one drug on a single medical device with or without an intervening polymer layer. For example, the present platform provides a dual drug eluting stent.

Some of the advantages provided by the coating process include employing compressed fluids (e.g., supercritical fluids, for example RESS based methods); solvent free deposition methodology; a platform that allows processing at lower temperatures thereby preserving the qualities of the active agent and the polymer matrix; the ability to incorporate two, three or more drugs while minimizing deleterious effects from direct interactions between the various drugs and/or their excipients during the fabrication and/or storage of the drug eluting stents; a dry deposition; enhanced adhesion and mechanical properties of the layers on the stent framework; precision deposition and rapid batch processing; and ability to form intricate structures.

The coating process may provide a multi-drug delivery platform which produces strong, resilient and flexible drug eluting stents including an anti-restenosis drug (e.g.; a limus or taxol) and anti-thrombosis drug (e.g.; heparin or an analog thereof) and well characterized bioabsorbable polymers. The drug eluting stents provided herein minimize potential for thrombosis, in part, by reducing or totally eliminating thrombogenic polymers and reducing or totally eliminating residual drugs that could inhibit healing.

Definitions

As used in the present specification, the following words and phrases are generally intended to have the meanings as set forth below, except to the extent that the context in which they are used indicates otherwise.

The terms "bioabsorbable," "biodegradable," "bioerodible," "bioresorbable," and "resorbable" are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbability of a polymer may be indicated in-vitro as described herein or by methods known to one of skill in the art. An in-vitro test for bioabsorbability of a polymer does not require living cells or other biologic materials to indicate bioabsorption properties (e.g. degradation, digestion). Thus, resorbtion, resorption, absorption, absorbtion, erosion may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

"Degradation" as used herein refers to the conversion or reduction of a chemical compound to one less complex, e.g., by splitting off one or more groups of atoms. Degradation of the coating may reduce the coating's cohesive and adhesive binding to the device, thereby facilitating transfer of the coating to the intervention site "Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs {NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, meberine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, timidazole, tioconazole, tioguanine, tioxolone, tiopramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. See, e.g., U.S. Pat. No. 6,897,205; see also U.S. Pat. Nos. 6,838,528; 6,497,729.

Examples of therapeutic agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

The active ingredients may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl) methacrylamide), Poly(1-aspartamide), etc.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof.

"Sintering" as used herein refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. As well, the sintering process is controlled such that some phase separation is obtained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer matrix. In embodiments involving incomplete sintering, a polymer matrix is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes autoxidation of drug, whether in amorphous, semi-crystalline, or crystalline form, by reducing exposure thereof to free radicals, residual solvents and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

The present invention provides several advantages which overcome or attenuate the limitations of current technology for bioabsorbable stents. For example, an inherent limitation of conventional bioabsorbable polymeric materials relates to the difficulty in forming to a strong, flexible, deformable (e.g. balloon deployable) stent with low profile. The polymers generally lack the strength of high-performance metals. The present invention overcomes these limitations by creating a laminate structure in the essentially polymeric stent. Without wishing to be bound by any specific theory or analogy, the increased strength provided by the stents of the invention can be understood by comparing the strength of plywood vs. the strength of a thin sheet of wood.

Embodiments of the invention involving a thin metallic stent-framework provide advantages including the ability to overcome the inherent elasticity of most polymers. It is generally difficult to obtain a high rate (e.g., 100%) of plastic deformation in polymers (compared to elastic deformation where the materials have some 'spring back' to the original shape). Again, without wishing to be bound by any theory, the central metal stent framework (that would be too small and weak to serve as a stent itself) would act like wires inside of a plastic, deformable stent, basically overcoming any 'elastic memory' of the polymer.

EXAMPLES

The following examples are given to enable those skilled in the art to more clearly understand and to practice the present invention. They should not be considered as limiting the scope of the invention, but merely as being illustrative and representative thereof. The following examples are provided to illustrate selected embodiments. They should not be considered as limiting the scope of the invention, but merely as being illustrative and representative thereof. Thus, the examples provided below, while illustrated with a particular medical device or active agent, are applicable to the range of medical devices and active agents described herein.

Polymer Stent

Example 1

Gel Spun Polymer Fibers

Spinning is manufacturing process for creating polymer fibers. It is a specialized form of extrusion that uses a spinneret to form multiple continuous filaments. First, the polymer being spun must be converted into a fluid state. If the polymer is a thermoplastic then it is just melted, if not then it may be dissolved in a solvent or chemically treated to form soluble or thermoplastic derivatives.

In this non-limiting example, the polymer material for the bioabsorbable stent is formed by gel spinning, also known as dry-wet spinning. The polymer is in a "gel" state, only partially liquid, which keeps the polymer chains somewhat bound together. These bonds produce strong inter-chain forces in the fiber, which increase its tensile strength. The polymer chains within the fibers also have a large degree of orientation, which increases strength.

The fluid polymer is then forced through the spinneret to form polymer filaments. The polymer filaments first pass through air and are cooled further in a liquid bath. This produces strong inter-chain forces in the resulting filaments that can significantly increase the tensile strength of the fibers. In addition, at least a portion of the polymer chains are aligned along the fiber axis by the shear forces during extrusion, which further enhances strength.

Example 2

Bioabsorbable Stent Formation

In this non-limiting example, the tubular scaffold of the present disclosure is made by forming a continuous wave form that includes a plurality of struts and a plurality of crowns. Each crown is a curved portion or turn within the wave form that connects adjacent struts to define the continuous wave form. In this example, the struts are substantially straight portions of the wave form 12. In other examples, the struts 18 are slightly bent or have other shapes, such as a sinusoidal wave, for example. The wave form may be formed by a single polymer fiber or filament or a plurality of interconnected polymer fibers or filaments.

After the wave form is formed, the wave form is wrapped around a mandrel, a center axis of which defines the longitudinal axis of the tubular scaffold. The wave form may be wrapped at an angle that is not perpendicular to the longitudinal axis to form a plurality of helical turns that together generally form a helical coil in the shape of a helix.

The tubular scaffold also includes a plurality of connections that are configured to connect selected crowns of adjacent turns. In this non-limiting example, the connections are be created by fusing the selected crowns together. As used herein, "fusing" is defined as heating the target portions of materials to be fused together, with or without adding any additional material, to a level where the material in the target portions flow together, intermix with one another, and form a fusion when the materials cool down to, for example, room temperature.

Example 3

Radial Strength Testing

This test is conducted to determine and graphically represent the change in stent internal diameter as a function of circumferential pressure and to determine the pressure at which deformation is no longer completely reversible for the disclosed stent. Fifteen (15) 3.0 mm and fifteen (15) 4.0 mm stents are subjected to all stent-manufacturing procedures. The stents are deployed to nominal pressure and removed from the delivery system. The stents are placed into a sleeve approximately 1 mm larger than the stent diameter. A vacuum is then applied and outer diameter measurements taken at various pressures. All samples should maintain a minimum of at least 50 percent of the nominal stent diameter after a 50 mm Hg pressure is applied.

Example 4

Stent Recoil Testing

This test is conducted to quantify the amount of elastic recoil. Fifteen (15) stent delivery systems of each length and diameter are subjected to all manufacturing and sterilization procedures. The stent delivery system is inflated to nominal pressure (e.g. 9ATM) and the stent is removed allowing for recoil to occur. The inner diameter at each end of the stent is recorded. Recoil is calculated subtracting the recoiled stent inner diameter from the pre-recoil inner diameter. Average recoil may ranged from 0.002 to 0.004 inches.

Example 5

Stent Expansion Testing

This test is conducted to determine if the plastic deformation experienced by the stent when expanded from the compressed profile to the final maximum deployed diameter can produce crack initiation for the disclosed stent. Fifteen (15) samples from each length and diameter are deployed to their largest possible diameters by inflating each delivery system to balloon failure. Each stent is examined at 45× magnification for potential cracks.

Example 6

Maximum Pressure (Burst Test) Testing

This test is conducted to demonstrate that the delivery system (with mounted stent) will not experience balloon, shaft, proximal adaptation or proximal/distal seal loss of integrity at or below the pressure required to expand the stent to its labeled diameter. Stent delivery systems that had been subjected to all manufacturing and sterilization procedures are pressurized to 90 psi with pressure held for 15 seconds and released for 3 seconds. The cycle is then repeated, increasing inflation pressure by 15 psi each cycle until failure.

Example 7

Analysis of the Strut Thickness

Scanning Electron Microscopy (SEM)

A sample coated stent described herein is obtained. Thickness of the device can be assessed using this analytical technique. The thickness of multiple struts were taken to ensure reproducibility and to characterize the coating and stent. The thickness of the coating was observed by SEM using a Hitachi S-4800 with an accelerating voltage of 800V. Various magnifications are used. SEM can provide top-down and cross-section images at various magnifications.

Nano X-Ray Computer Tomography

Another technique that may be used to view the physical structure of a device in 3-D is Nano X-Ray Computer Tomography (e.g. such as made by SkyScan).

Example 8

Determination of the Bioabsorbability of a Device

Techniques presented with respect to showing Bioabsorbability of a polymer coating may be used to additionally and/or alternatively show the bioabsorbability of a device, for example, by GPC In-Vivo testing, HPLC In-Vivo Testing, GPC In-Vitro testing, HPLC In-Vitro Testing, SEM-FIB Testing, Raman Spectroscopy, SEM, and XPS as described herein with variations and adjustments which would be obvious to those skilled in the art. Another technique to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorbtion.

Drug Elution Polymer Stent

Example 11

Determination of an Elution Profile

In Vitro

In one method, a stent described herein is obtained. The elution profile is determined as follows: stents are placed in 16 mL test tubes and 15 mL of 10 mM PBS (pH 7.4) is pipetted on top. The tubes are capped and incubated at 37 C with end-over-end rotation at 8 rpm. Solutions are then collected at the designated time points (e.g. 1 d, 7 d, 14 d, 21 d, and 28 d) (e.g. 1 week, 2 weeks, and 10 weeks) and replenished with fresh 1.5 ml solutions at each time point to prevent saturation. One mL of DCM is added to the collected sample of buffer and the tubes are capped and shaken for one minute and then centrifuged at 200.times.G for 2 minutes. The supernatant is discarded and the DCM phase is evaporated to dryness under gentle heat (40.degree. C.) and nitrogen gas. The dried DCM is reconstituted in 1 mL of 60:40 acetonitrile:water (v/v) and analyzed by HPLC. HPLC analysis is performed using Waters HPLC system (mobile phase 58:37:5 acetonitrile:water:methanol 1 mL/min, 20 uL injection, C18 Novapak Waters column with detection at 232 nm).

In another method, the in vitro pharmaceutical agent elution profile is determined by a procedure comprising contacting the device with an elution media comprising ethanol (5%) wherein the pH of the media is about 7.4 and wherein the device is contacted with the elution media at a temperature of about 37.degree. C. The elution media containing the device is optionally agitating the elution media during the contacting step. The device is removed (and/or the elution media is removed) at least at designated time points (e.g. 1 h, 3 h, 5 h, 7 h, 1 d, and daily up to 28 d) (e.g. 1 week, 2 weeks, and 10 weeks). The elution media is then assayed using a UV-Vis for determination of the pharmaceutical agent content. The elution media is replaced at each time point with fresh elution media to avoid saturation of the elution media. Calibration standards containing known amounts of drug were also held in elution media for the same durations as the samples and used at each time point to determine the amount of drug eluted at that time (in absolute amount and as a cumulative amount eluted).

In another method, the in vitro pharmaceutical agent elution profile is determined by a procedure comprising contacting the device with an elution media comprising ethanol (20%) and phosphate buffered saline (80%) wherein the pH of the media is about 7.4 and wherein the device is contacted with the elution media at a temperature of about 37.degree. C. The elution media containing the device is optionally agitating the elution media during the contacting step. The device is removed (and/or the elution media is removed) at least at designated time points (e.g. 1 h, 3 h, 5 h, 7 h, 1 d, and daily up to 28 d) (e.g. 1 week, 2 weeks, and 10 weeks). The elution media is replaced periodically (at least at each time point, and/or daily between later time points) to prevent saturation; the collected media are pooled together for each time point. The elution media is then assayed for determination of the pharmaceutical agent content using HPLC. The elution media is replaced at each time point with fresh elution media to avoid saturation of the elution media. Calibration standards containing known amounts of drug are also held in elution media for the same durations as the samples and used at each time point to determine the amount of drug eluted at that time (in absolute amount and as a cumulative amount eluted). Where the elution method changes the drug over time, resulting in multiple peaks present for the drug when tested, the use of these calibration standards will also show this change, and allows for adding all the peaks to give the amount of drug eluted at that time period (in absolute amount and as a cumulative amount eluted).

To obtain an accelerated in-vitro elution profile, an accelerated elution buffer comprising 18% v/v of a stock solution of 0.067 mol/L $KH_2PO_4$ and 82% v/v of a stock solution of 0.067 mol/L Na2HPO4 with a pH of 7.4 is used. Stents described herein are expanded and then placed in 1.5 ml solution of this accelerated elution in a 70 degree Celsius bath with rotation at 70 rpm. The solutions are then collected at the following time points: 0 min, 15 min., 30 min., 1 hr, 2 hr, 4 hr, 6 hr, 8 hr, 12 hr, 16 hr, 20 hr, 24 hr, 30 hr, 36 hr and 48 hr. Fresh accelerated elution buffer are added periodically at least at each time point to replace the incubated buffers that are collected and saved in order to prevent saturation. For time points where multiple elution media are used (refreshed between time points), the multiple collected solutions are pooled together for liquid extraction by dichloromethane. Dichloromethane extraction and HPLC analysis is performed in the manner described previously.

In Vivo

Rabbit in vivo models as described above are euthanized at multiple time points. Stents are explanted from the rabbits. The explanted stents are placed in 16 mL test tubes and 15 mL of 10 mM PBS (pH 7.4) is pipette on top. One mL of DCM is added to the buffer and the tubes are capped and shaken for one minute and then centrifuged at 200.times.G for 2 minutes. The supernatant is discarded and the DCM phase is evaporated to dryness under gentle heat (40.degree. C.) and nitrogen gas. The dried DCM is reconstituted in 1 mL of 60:40 acetonitrile:water (v/v) and analyzed by HPLC. HPLC analysis is performed using Waters HPLC system (mobile phase 58:37:5 acetonitrile:water: methanol 1 mL/min, 20 uL injection, C18 Novapak Waters column with detection at 232 nm).

Example 12

Crystallinity of Drug

The presence and or quantification of the active agent crystallinity can be determined from a number of characterization methods known in the art, but not limited to, XRPD, vibrational spectroscopy (FTIR, NIR, Raman), polarized optical microscopy, calorimetry, thermal analysis and solid-state NMR.

X-Ray Diffraction to Determine the Presence and/or Quantification of Active Agent Crystallinity Active agent and polymer coated proxy substrates are prepared using 316L stainless steel coupons for X-ray powder diffraction (XRPD) measurements to determine the presence of crystallinity of the active agent. The coating on the coupons is equivalent to the coating on the stents described herein. Coupons of other materials described herein, such as cobalt-chromium alloys, may be similarly prepared and tested. Likewise, substrates such as stents, or other medical devices described herein may be prepared and tested. Where a coated stent is tested, the stent may be cut lengthwise and opened to lay flat in a sample holder.

For example XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation (e.g.; Wide Angle X-ray Scattering or WAXS), for example, as described in F. Unger, et al., "Poly(ethylene carbonate): A thermoelastic and biodegradable biomaterial for drug eluting stent coatings?" Journal of Controlled Release, Volume 117, Issue 3, 312-321 (2007) for which the technique and variations of the technique specific to a particular sample would be obvious to one of skill in the art.

Raman Spectroscopy

Raman spectroscopy, a vibrational spectroscopy technique, can be useful, for example, in chemical identification, characterization of molecular structures, effects of bonding, identification of solid state form, environment and stress on a sample. Raman spectra can be collected from a very small volume (<1 µm³); these spectra allow the identification of species present in that volume. Spatially resolved chemical information, by mapping or imaging, terms often used interchangeably, can be achieved by Raman microscopy.

Raman spectroscopy and other analytical techniques such as described in Balss, et al., "Quantitative spatial distribution of sirolimus and polymers in drug-eluting stents using confocal Raman microscopy" J. of Biomedical Materials Research Part A, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

For example, to test a sample using Raman microscopy and in particular confocal Raman microscopy, it is understood that to get appropriate Raman high resolution spectra sufficient acquisition time, laser power, laser wavelength, sample step size and microscope objective need to be optimized. For example a sample (a coated stent) is prepared as described herein. Alternatively, a coated coupon could be tested in this method. Maps are taken on the coating using Raman microscopy. A WITec CRM 200 scanning confocal Raman microscope using a Nd:YAG laser at 532 nm is applied in the Raman imaging mode. The laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 seconds of integration time. Each confocal cross-sectional image of the coatings displays a region 70 µm wide by 10 µm deep, and results from the gathering of 6300 spectra with a total imaging time of 32 min.

Multivariate analysis using reference spectra from samples of rapamycin (amorphous and crystalline) and polymer are used to deconvolve the spectral data sets, to provide chemical maps of the distribution.

Infrared (IR) Spectroscopy for In-Vitro Testing

Infrared (IR) Spectroscopy such as FTIR and ATR-IR are well utilized techniques that can be applied to show, for example, the quantitative drug content, the distribution of the drug in the sample coating, the quantitative polymer content in the coating, and the distribution of polymer in the coating. Infrared (IR) Spectroscopy such as FTIR and ATR-IR can similarly be used to show, for example, drug crystallinity. The following table lists the typical IR materials for various applications. These IR materials are used for IR windows, diluents or ATR crystals.

of fusion at or about 46.8 J/g). The heat of fusion decreases with the percent crystallinity. Thus, the degree of crystallinity could be determined relative to a pure sample, or versus a calibration curve created from a sample of amorphous drug spiked and tested by DSC with known amounts of crystalline drug. Presence (at least) of crystalline drug on a stent could be measured by removing (scraping or stripping) some drug from the stent and testing the coating using the DSC equipment for determining the melting temperature and the heat of fusion of the sample as compared to a known standard and/or standard curve.

Confocal Raman Microscopy

Confocal Raman Microscopy can provide nondestructive depth analysis and allows coating specific Raman spectral features to be obtained (Bugay et al., "Raman Analysis of Pharmaceuticals," in "*Applications of Vibrational Spectroscopy in Pharmaceutical Research and Development*," Ed. Pivonka, D. E., Chalmers, J. M., Griffiths, P. R. (2007) Wiley and Sons). In confocal Raman microscopy an aperture is place in a focal place of the collected beam. This limitation defines a shallow portion of the depth of field and thereby provides definition of the z-axis spatial resolution for data collection. By adjusting the aperture and moving the focus within the sample, the sampling position within the sample moves. Moving the sample focus from the top surface, deeper into the specimen facilitates nondestructive depth analysis.

Example 13

Coating Uniformity

The ability to uniformly coat devices, e.g., pre- and post-expansion stents, and balloons, with controlled composition and thickness using electrostatic capture in a rapid expansion of supercritical solution (RESS) experimental series has been demonstrated.

Scanning Electron Microscopy (SEM)

Devices are observed by SEM using a Hitachi S-4800 with an accelerating voltage of 800V. Various magnifications

| MATERIAL | NACL | KBR | CSI | AGCL | GE | ZNSE | DIAMOND |
|---|---|---|---|---|---|---|---|
| Transmission range (cm−1) | 40,000~625 | 40,000~400 | 40,000~200 | 25,000~360 | 5,500~625 | 20,000~454 | 40,000~2,500 & 1667-33 |
| Water sol (g/100 g, 25 C.) | 35.7 | 53.5 | 44.4 | Insol. | Insol. | Insol. | Insol. |
| Attacking materials | Wet Solvents | Wet Solvents | Wet Solvents | Ammonium Salts | H2SO4, aqua regin | Acids, strong alkalies, chlorinated solvents | K2Cr2Os, conc. H2SO4 |

In one test, a coupon of crystalline ZnSe is coated by the processes described herein, creating a PDPDP (Polymer, Drug, Polymer, Drug, Polymer) layered coating that is about 10 microns thick. The coated coupon is analyzed using FTIR. The resulting spectrum shows crystalline drug as determined by comparison to the spectrum obtained for the crystalline form of a drug standard (i.e. a reference spectrum).

Differential Scanning Calorimetry (DSC)

DSC can provide qualitative evidence of the crystallinity of the drug (e.g. rapamycin) using standard DSC techniques obvious to one of skilled in the art. Crystalline melt can be shown using this analytical method (e.g. rapamycin crystalline melting—at about 185° C. to 200° C., and having a heat are used to evaluate the integrity, especially at high strain regions. SEM can provide top-down and cross-section images at various magnifications. Coating uniformity and thickness can also be assessed using this analytical technique.

Pre- and post-inflation balloons, for example, may be observed by SEM using a Hitachi S-4800 with an accelerating voltage of 800V. Various magnifications may be used to evaluate the integrity of the layers, and or of the coating.

Scanning Electron Microscopy (SEM) with Focused Ion Beam (FIB)

Devices as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible.

Optical Microscopy

An optical microscope may be used to create and inspect the devices and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformality and for evidence of crystallinity of the drug.

Example 14

Total Drug Content on Coated Stent (Used or Unused)

Determination of the total content of the active agent in a coated substrate may be tested using techniques described herein as well as other techniques obvious to one of skill in the art, for example using GPC and HPLC techniques to extract the drug from the coated substrate and determine the total content of drug in the sample.

UV-VIS can be used to quantitatively determine the mass of rapamycin (or another active agent) coated onto the substrates. A UV-Vis spectrum of Rapamycin can be shown and a Rapamycin calibration curve can be obtained, (e.g. λ@ 277 nm in ethanol). Rapamycin is then dissolved from the coated substrate in ethanol, and the drug concentration and mass calculated.

In one test, the total amount of rapamycin (or another active agent) present in units of micrograms per substrate is determined by reverse phase high performance liquid chromatography with UV detection (RP-HPLC-UV). The analysis is performed with modifications of literature-based HPLC methods for rapamycin (or the other active agent) that would be obvious to a person of skill in the art. The average drug content of samples (n=10) from devices comprising stents and coatings as described herein, and/or methods described herein are tested.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A biomedical implant, comprising:
a tubular scaffold comprising a plurality of interconnected bioabsorbable polymer struts, the interconnected polymer struts defining a plurality of deformable cells, said polymer struts including polymer chains that are longitudinally aligned along the axis of said polymer struts, and wherein the tubular scaffold has an average axial elastic modulus along an axis of the tubular scaffold and an average circumferential elastic modulus orthogonally surrounding the axis of the tubular scaffold, the average circumferential elastic modulus being greater than the average axial elastic modulus; and
a pharmaceutical agent admixed with the bioabsorbable polymer struts of the implant in a manner which does not affect the structural and morphological integrity of the pharmaceutical agent, the pharmaceutical agent being a macrolide immunosuppressant drug in crystalline form,
wherein the polymer struts have an average thickness of no more than 120 μm and wherein the pharmaceutical agent is dispersed within and evenly distributed throughout the volume of the polymer struts such that the entirety of the implant is bioabsorbable.

2. The biomedical implant of claim 1, wherein the tubular scaffold maintains at least 50% of its nominal luminal cross sectional area under a pressure load of 50 mmHg.

3. The biomedical implant of claim 1, wherein at least 80% of the polymer struts are bioabsorbed within 2 years after deployment in vivo.

4. The biomedical implant of claim 1, wherein the polymer struts comprises a polymer material selected from the group consisting of polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof.

5. The biomedical implant of claim 1, wherein the macrolide immunosuppressant is selected from the group consisting of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy] ethyl-rapamycin, 40-O-[(3S)-2,2-Dimethyldioxolan-3-yl] methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino) acetoxy]ethyl-rapamycin, 40-O-(2-N-Imidazolylacetoxy) ethyl-rapamycin, 40-O-[2-(N-Methyl-N'-piperazinyl) acetoxy]ethyl-rapamycin, 39-O-Desmethyl-39,40-O,O-ethylene-rapamycin, (26R)-26-Dihydro-40-O-(2-hydroxy) ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]- rapamycin, 42-Epi-(tetrazolyl)rapamycin (tacrolimus), and 42-[3-hydroxy-2-(hydroxymethyl)-2-methylpropanoate]rapamycin.

6. The biomedical implant of claim 1, wherein the pharmaceutical agent is rapamycin.

7. The biomedical implant of claim 1, wherein at least a portion of the tubular scaffold is covered with a coating comprising a second pharmaceutical agent.

8. The biomedical implant of claim 1, wherein the tubular scaffold has an average axial elastic modulus along an axis of the tubular scaffold and an average circumferential elastic modulus orthogonally surrounding the axis of the tubular scaffold, the average circumferential elastic modulus being greater than the average axial elastic modulus.

* * * * *